(12) United States Patent
Cai et al.

(10) Patent No.: US 6,559,163 B2
(45) Date of Patent: May 6, 2003

(54) 2,4-SUBSTITUTED QUINOLINE DERIVATIVES

(75) Inventors: Guolin Cai, Thousand Oaks, CA (US); Jun Yuan, Guilford, CT (US); Kevin Currie, North Branford, CT (US); Pamela Albaugh, Carmel, IN (US); Alan Hutchison, Madison, CT (US)

(73) Assignee: Neurogen Corporation, Brandford, CT (US)

( * ) Notice: Subject to any disclaimer, the term of this patent is extended or adjusted under 35 U.S.C. 154(b) by 0 days.

(21) Appl. No.: 09/931,549

(22) Filed: Aug. 16, 2001

(65) Prior Publication Data

US 2002/0161008 A1 Oct. 31, 2002

Related U.S. Application Data

(60) Provisional application No. 60/225,552, filed on Aug. 16, 2000.

(51) Int. Cl.$^7$ ............... A61K 31/4709; A61K 31/4725; C07D 215/116
(52) U.S. Cl. ................. 514/314; 546/168; 546/175
(58) Field of Search ................. 546/168, 175; 514/314

(56) References Cited

U.S. PATENT DOCUMENTS

| 4,711,890 A | * | 12/1987 | Dubroeucq et al. ......... 514/311 |
| 6,103,905 A | | 8/2000 | Cuny et al. |

FOREIGN PATENT DOCUMENTS

| EP | 0 112 776 A | 7/1984 |
| WO | WO 98/50346 | 11/1998 |
| WO | WO 98/57931 | 12/1998 |

OTHER PUBLICATIONS

M.T. Ngyen, H. Le Trong: "Synthesis and reactions of atophan analogs containing an indole ring system. III. Synthesis of some 2–(3–indolyl)cinchoninic acid derivatives", Database Caplus 'Online!, Chemical Abstracts Service, Columbus, Ohio, U.S.; AN=530575, 1984.

* cited by examiner

Primary Examiner—Alan L. Rotman
Assistant Examiner—Rita Desai
(74) Attorney, Agent, or Firm—McDonnell Boehnen Hulbert & Berghoff

(57) ABSTRACT

Disclosed are compounds of the formula

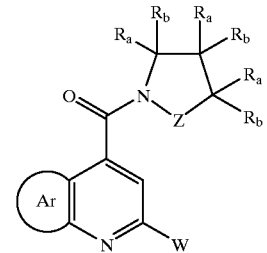

or pharmaceutically acceptable salts thereof wherein:

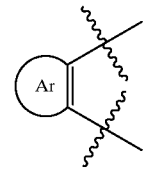

represents:

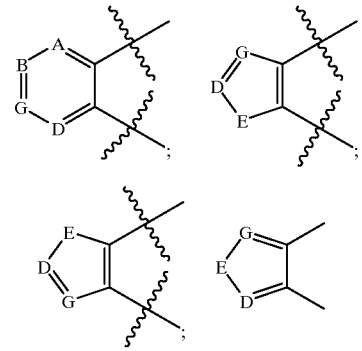

and A, B, G, D, E, $R_a$, $R_b$, W, and Z are defined herein. These compounds are agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Down Syndrome, sleep and seizure disorders, overdose with benzodiazepine drugs and for enhancement of memory. Pharmaceutical compositions, including packaged pharmaceutical compositions, are further provided. Compounds of the invention are also useful as probes for the localization of $GABA_A$ receptors in tissue samples.

31 Claims, No Drawings

2,4-SUBSTITUTED QUINOLINE DERIVATIVES

This application claims priority from U.S. Provisional Application Ser. No. 60/225,552, filed Aug. 16, 2000.

BACKGROUND OF THE INVENTION

1. Field of the Invention

This invention relates to heterocyclic derivatives, especially quinoline carbonyl pyrrolidines that bind with high selectivity and high affinity to the benzodiazepine site of $GABA_A$ receptors. This invention also relates to pharmaceutical compositions comprising such compounds and to the use of such compounds in treatment of central nervous system (CNS) diseases. This invention also relates to the use of these heterocyclic compounds in combination with one or more other CNS agents to potentiate the effects of the other CNS agents. Additionally this invention relates to the use such compounds as probes for the localization of $GABA_A$ receptors in tissue sections.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg Science 1989; 245:1389–1392 and Knight et. al., Recept. Channels 1998; 6:1–18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

This invention provides heterocyclic compounds, especially quinoline carbonyl pyrrolidines that bind to the benzodiazepine site of the $GABA_A$ receptor, including human $GABA_A$ receptors.

Thus, the invention provides compounds of Formula I (shown below), and pharmaceutical compositions comprising compounds of Formula I.

The invention further comprises methods of treating patients suffering from CNS disorders with an effective amount of a compound of the invention. The patient may be a human or other mammal. Treatment of humans, domesticated companion animals (pets) or livestock animals suffering from CNS disorders with a therapeutically effective amount of a compound of the invention is encompassed by the invention.

In a separate aspect, the invention provides a method of potentiating the actions of other CNS active compounds. This method comprises administering a therapeutically effective amount of a compound of the invention with another CNS active compound.

Additionally this invention relates to the use of the compounds of the invention as probes for the localization of $GABA_A$ receptors, for example, in tissue sections.

Accordingly, a broad aspect of the invention is directed to compounds of Formula I:

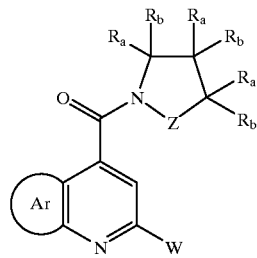

Formula I or a pharmaceutically acceptable salt thereof wherein:

represents:

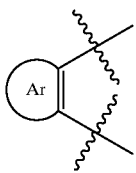

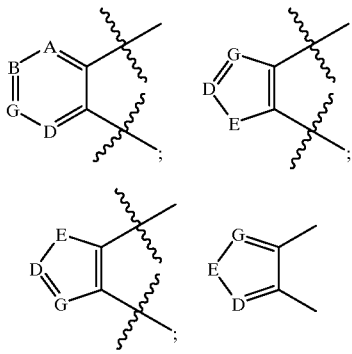

wherein:

A, B, D, and G are nitrogen or C—$R_1$;

with the proviso that not more than 2 of A, B, G, and D are nitrogen; and

E represents oxygen, sulfur or N—$R_5$;

$R_1$ at each occurrence is independently selected from the group consisting of hydrogen, halogen, cyano, haloalkylhaloalkoxy, hydroxy, amino, —NH($R_2$), —N($R_2$)$_2$, nitro, $C_1$–$C_8$ alkoxy and $R_2$; wherein $R_2$ at each occurrence is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloalkenyl, and $C_5$–$C_{10}$ cycloalkynyl, $R_5$ is selected from the group consisting of $R_2$, aryl, and $C_1$–$C_8$ alkoxy$_1$, wherein $R_2$, the aryl group and the $C_1$–$C_8$ alkoxy$_1$, are optionally substituted with 1, 2, 3, or 4 groups selected from the group consisting of hydroxy, cyano, halogen, nitro, haloalkyl, haloalkoxy, amino, —NH($R_2$), and —N($R_2$)$_2$;

$R_a$ and $R_b$ at each occurrence are independently selected from the group consisting of hydrogen, halogen, cyano, nitro, haloalkyl, haloalkoxy, hydroxy, amino, —O$R_2$ wherein $R_2$ is substituted with 0–2 $R_6$, —NH($R_2$) wherein $R_2$ is substituted with 0–2 $R_6$, —N($R_2$)$_2$ wherein the $R_2$ groups are independently substituted with 0–2 $R_6$, substituted with 0–2 $R_6$, phenyl substituted with 0–3 $R_6$, —X$R_7$, and Y;

W represents phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, or quinoxalinyl, wherein each is substituted with $R_d$, $R_{d'}$, and $R_{d''}$ which are independently selected from the group consisting of hydrogen, halogen, cyano, nitro, haloalkyl, haloalkoxy, hydroxy, amino, $R_2$ substituted with 0–2 $R_6$, —O$R_2$ substituted with 0–2 $R_6$, —NH($R_2$) wherein $R_2$ is substituted with 0–2 $R_6$, phenyl substituted with 0–3 $R_6$, —X$R_7$, Y, and —N($C_1$–$C_6$ alkyl$_1$) ($C_1$–$C_6$ alkyl$_2$) where each alkyl is independently substituted with 0–2 $R_6$, or alkyl$_1$, alkyl$_2$ and the nitrogen to which they are attached form a heterocycloalkyl ring substituted with 0–2 $R_6$;

X at each occurrence is independently selected from the group consisting of —CH$_2$—, —CHR$_8$—, —O—, —S(O)$_m$—, —NH—, —NR$_8$—, —C(O)—, —C(O)O—, —C(O)NH—, —C(O)NR$_8$—, —S(O)$_m$NH—, —S(O)$_m$NR$_8$—, —NHC(O)—, —NR$_8$C(O)—, —NHS(O)$_m$—, and —NR$_8$S(O)$_m$—; wherein m is 0, 1, or 2;

$R_6$ at each occurrence is independently selected from the group consisting of halogen, hydroxy, $R_2$, —O$R_2$, —NH($R_2$), —N($R_2$)$_2$, —NH—($R_2$—Y), —N($R_2$)—($R_2$—Y), —NH—($R_2$—N($R_2$)($R_2$)), —N($R_2$)—($R_2$—N($R_2$))($R_2$) morpholinyl, pyrrolidinyl, piperidinyl, thiomorpholinyl, piperazinyl, homopiperazinyl, —S(O)$_m$($R_2$), haloalkyl, haloalkoxy, —CO($R_2$), —CONH($R_2$), CON($R_2$)$_2$, —X$R_7$, and Y;

wherein m is 0, 1, or 2;

$R_7$ and $R_8$ at each occurrence independently carry the same definition as $R_2$, wherein $R_7$ and $R_8$ are substituted with 0, 1, 2, 3, or 4 substituents selected from the group consisting of oxo, hydroxy, halogen, amino, cyano, nitro, haloalkyl, haloalkoxy, —O($R_2$), —NH($R_2$), —N($R_2$)$_2$, —NHC(O) ($R_2$), —N($R_2$)C(O) ($R_2$), —NHS(O)$_m$($R_2$), —S(O)$_m$($R_2$), —S(O)$_m$NH($R_2$), and —S(O)$_m$N($R_2$)$_2$, and Y';

wherein m is 0, 1, or 2;

Y and Y' at each occurrence are independently selected from 5- to 8-membered carbocycles or heterocycles, which are saturated partially unsaturated, or aromatic and contain zero, one or two heteroatoms selected from N, O, and S, which carbocycles or heterocycles may be further substituted with 1, 2, 3, or 4 substituents selected from the group consisting of halogen, oxo, hydroxy, amino, nitro, cyano, $R_2$, —O$R_2$, —NH($R_2$), —N($R_2$)$_2$, and —S(O)$_a$($R_2$); wherein a is 0, 1, or 2; and Z is (CR$_a$R$_b$)$_n$, wherein n is 0, 1, or 2.

The invention further provides methods for making the compounds of Formula I as well as intermediates useful in those methods.

DETAILED DESCRIPTION OF THE INVENTION

Preferred compounds of Formula I are those where W is phenyl carrying $R_d$, $R_{d'}$, and $R_{d''}$ where one of $R_d$, $R_{d'}$, and $R_{d''}$ is hydrogen and the other two are are independently hydrogen, halogen, hydroxy, $C_1$–$C_6$ alkylamino($C_1$–$C_6$) alkoxy, $C_1$–$C_6$ or alkoxy. Still other preferred compounds of Formula I are those where A, B, G, and D are CR$_1$ and W is phenyl substituted with $R_d$, $R_{d'}$, and $R_{d''}$ where one of $R_d$, $R_{d'}$, and $R_{d''}$ is hydrogen and the other two are are independently hydrogen, halogen, hydroxy, $C_1$–$C_6$ alkylamino ($C_1$–$C_6$)alkoxy, $C_1$–$C_6$ or alkoxy.

A group of preferred compounds of Formula I designated as compounds of Formula Ia herein are those wherein:

A, B, D, and G are nitrogen or C—$R_1$;

with the proviso that not more than 2 of A, B, G, and D are nitrogen; and

E represents oxygen, sulfur or N—R$_5$;

R$_1$ at each occurrence is independently selected from the group consisting of hydrogen, C$_1$–C$_6$ alkyl, halogen, cyano, Haloalkyl, haloalkoxy, hydroxy, amino, —NH(C$_1$–C$_6$ alkyl), and —N(C$_1$–C$_6$ alkyl) (C$_1$–C$_6$ alkyl);

R$_5$ is selected from the group consisting of C$_1$–C$_6$ alkyl, aryl, and C$_1$–C$_6$ alkoxy, wherein the C$_1$–C$_6$ alkyl, the aryl group, and the C$_1$–C$_6$ alkoxy are optionally substituted with 1, 2, 3, or 4 groups selected from the group consisting of hydroxy, cyano, halogen, nitro, haloalkyl, haloalkoxy, amino, —NH(C$_1$–C$_6$ alkyl), and —N(C$_1$–C$_6$ alkyl) (C$_1$–C$_6$ alkyl);

R$_a$ and R$_b$ at each occurrence are independently selected from the group consisting of hydrogen, halogen, cyano, nitro, haloalkyl, haloalkoxy; hydroxy, amino, C$_1$–C$_6$ alkoxy substituted with 0–2 R$_6$, —NH(C$_1$–C$_6$ alkyl) substituted with 0–2 R$_6$, —N(C$_1$–C$_6$ alkyl) (C$_1$–C$_6$ alkyl) wherein the C$_1$–C$_6$ alkyl groups are independently substituted with 0–2 R$_6$, C$_1$–C$_6$ alkyl wherein the C$_1$–C$_6$ alkyl group is substituted with 0–2 R$_6$, phenyl substituted with 0–3 R$_6$, —XR$_7$, and Y;

W represents phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, or quinoxalinyl, wherein each is substituted with R$_d$, R$_{d'}$, and R$_{d''}$ which are independently selected from the group consisting of hydrogen, halogen, cyano, nitro, haloalkyl, haloalkoxy, hydroxy, amino, C$_1$–C$_6$ alkyl substituted with 0–2 R$_6$, C$_1$–C$_6$ alkoxy substituted with 0–2 R$_6$, —NH(C$_1$–C$_6$ alkyl) wherein the C$_1$–C$_6$ alkyl is substituted with 0–2 R$_6$, phenyl substituted with 0–3 R$_6$, —XR$_7$, Y, and —N(C$_1$–C$_6$ alkyl$_1$) (C$_1$–C$_6$ alkyl$_2$) wherein alkyl$_1$ and alkyl$_2$ are independently substituted with 0–2 R$_6$, or alkyl$_1$, alkyl$_2$ and the nitrogen to which they are attached form a heterocycloalkyl ring substituted with 0–2 R$_6$;

X at each occurrence is independently selected from the group consisting of —CH$_2$—, —CHR$_8$—, —O—, —S(O)$_m$—, —NH—, —NR$_8$—, —C(O)—, —C(O)O—, —C(O)NH—, —C(O)NR$_8$—, —S(O)$_m$NH—, —S(O)$_m$NR$_8$—, —NHC(O)—, —NR$_8$C(O)—, —NHS(O)$_m$—, and —NR$_8$S(O)$_m$—; wherein m is 0, 1, or 2;

R$_6$ at each occurrence is independently selected from the group consisting of halogen, hydroxy, C$_1$–C$_6$ alkyl, C$_1$–C$_6$ alkoxy, —NH(C$_1$–C$_6$ alkyl), —N(C$_1$–C$_6$ alkyl) (C$_1$–C$_6$ alkyl), —NH—(C$_1$–C$_6$ alkyl-Y), —N(C$_1$–C$_6$ alkyl)—(C$_1$–C$_6$ alkyl-Y), —NH—(C$_1$–C$_6$ alkyl—N(C$_1$–C$_6$ alkyl) (C$_1$–C$_6$ alkyl)), —N(C$_1$–C$_6$ alkyl)—(C$_1$–C$_6$ alkyl-N(C$_1$–C$_6$ alkyl) (C$_1$–C$_6$ alkyl)), morpholinyl, pyrrolidinyl, piperidinyl, thiomorpholinyl, piperazinyl, homopiperazinyl, —S(O)$_m$(C$_1$–C$_6$ alkyl), haloalkyl, haloalkoxy, —CO(C$_1$–C$_6$ alkyl), —CONH(C$_1$–C$_6$ alkyl), CON(C$_1$–C$_6$ alkyl) (C$_1$–C$_6$ alkyl), —XR$_7$, and Y; wherein m is 0, 1, or 2;

R$_7$ and R$_8$ at each occurrence are independently C$_1$–C$_8$ alkyl, wherein R$_7$ and R$_8$ are substituted with 0, 1, 2, 3, or 4 substituents selected from the group consisting of oxo, hydroxy, halogen, amino, cyano, nitro, trifluoromethyl, trifluoromethoxy, C$_1$–C$_6$ alkoxy, —NH(C$_1$–C$_6$ alkyl), —N(C$_1$–C$_6$ alkyl) (C$_1$–C$_6$ alkyl), —NHC(O) (C$_1$–C$_6$ alkyl), —N(C$_1$–C$_6$ alkyl)C(O) (C$_1$–C$_6$ alkyl), —NHS(O)$_m$(C$_1$–C$_6$ alkyl), —S(O)$_m$(C$_1$–C$_6$ alkyl), —S(O)$_m$NH(C$_1$–C$_6$ alkyl), and —S(O)$_m$N(C$_1$–C$_6$ alkyl) (C$_1$–C$_6$ alkyl), and Y';

wherein m is 0, 1, or 2; and

Y and Y' at each occurrence are independently selected from 5- to 8-membered carbocycles or heterocycles, which are saturated, partially unsaturated, or aromatic, and contain zero, one or two heteroatoms selected from N, O, and S, and which carboxycles or heterocycles may be further substituted with 1, 2, 3, or 4 substituents selected from the group consisting of halogen, oxo, hydroxy, amino, nitro, cyano, C$_1$–C$_6$ alkyl, C$_1$–C$_6$ alkoxy, —NH(C$_1$–C$_6$ alkyl), —N(C$_1$–C$_6$ alkyl) (C$_1$–C$_6$ alkyl), and —S(O)$_a$(C$_1$–C$_6$ alkyl); wherein a is 0, 1, or 2; and Z is (CR$_a$R$_b$)$_n$, wherein n is 0, 1, or 2.

Preferred compounds of Formula Ia are those where A, B, G, and D are CR$_1$ and W is phenyl is substituted with R$_d$, R$_{d'}$, and R$_{d''}$, where one of R$_d$, R$_{d'}$, and R$_{d''}$ is hydrogen and the other two are are independently hydrogen, halogen, hydroxy, C$_1$–C$_6$ alkylamino(C$_1$–C$_6$)alkoxy, C$_1$–C$_6$ or alkoxy.

Still other preferred compounds of Formula Ia include those where W is phenyl para substituted with C$_1$–C$_6$ alkylamino (C$_1$–C$_6$)alkoxy. Another preferred group of compounds of Formula Ia are those where W is phenyl or thienyl, more preferably phenyl, each of which is optionally mono- of disubstituted with groups independently selected from C$_1$–C$_6$ alkyl, C$_1$–C$_6$ alkoxy, halogen, hydroxy, C$_1$–C$_6$ alkylamino (C$_1$–C$_6$)alkoxy, and C$_1$–C$_6$ alkoxy. More preferably, the phenyl and thienyl groups are mono- or disubstituted with C$_1$–C$_2$ alkyl, C$_1$–C$_2$ alkoxy, halogen, preferably chloro or fluoro, hydroxy, mono- or di(C$_1$–C$_2$) alkylamino(C$_1$–C$_2$)alkoxy, and C$_1$–C$_6$ alkoxy.

A preferred subclass of compounds of the invention is represented by compounds of Formula II, and the salts, prodrugs, and solvates thereof:

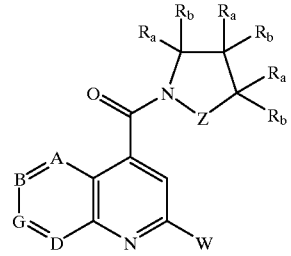

Formula II wherein A, B, G, D, R$_a$, R$_b$, W, and Z are defined as in Formula I.

Preferred compounds of Formula II include those where A, B, G, and D are CR$_1$. Other preferred compounds of Formula II are those where A, B, G, and D are CR$_1$ and W is phenyl is substituted with R$_d$, R$_{d'}$, and R$_{d''}$, where one of R$_d$, R$_{d'}$, and R$_{d''}$ is hydrogen and the other two are are independently hydrogen, halogen, hydroxy, C$_1$–C$_6$ alkylamino(C$_1$–C$_6$)alkoxy, C$_1$–C$_6$ or alkoxy.

Still other preferred compounds of Formula II include those where W is phenyl para substituted with C$_1$–C$_6$ alkylamino(C$_1$–C$_6$)alkoxy. Another preferred group of compounds of Formula II are those where W is phenyl or thienyl, more preferably phenyl, each of which is optionally mono- of disubstituted with groups independently selected from $C_1$–$C_6$ alkyl, $C_1$–$C_6$ alkoxy, halogen, hydroxy, $C_1$–$C_6$ alkylamino($C_1$–$C_6$)alkoxy, and $C_1$–$C_6$ alkoxy. More preferably, the phenyl and thienyl groups are mono- or disubstituted with $C_1$–$C_2$ alkyl, $C_1$–$C_2$ alkoxy, halogen, preferably chloro or fluoro, hydroxy, mono- or di($C_1$–$C_2$) alkylamino($C_1$–$C_2$)alkoxy, and $C_1$–$C_6$ alkoxy.

More preferred compounds of Formula II, include compounds of Formula IIa:

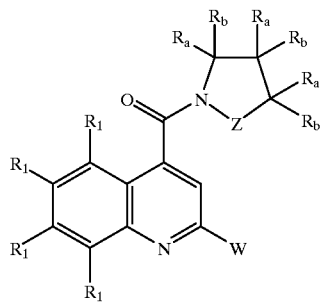

Formula IIa and the pharmaceutically acceptable salts thereof, wherein $R_1$, $R_a$, $R_b$, W, and Z are defined as in for Formula I.

Particular compounds of Formula IIa are those compounds where W is phenyl or thienyl, substituted with $R_d$, $R_{d'}$, $R_{d''}$, which are defined as in Formula I. Preferred $R_1$ groups in Formula IIa include hydrogen, halogen, cyano, trifluoromethyl, trifluoromethoxy, hydroxy, amino, mono- and di($C_1$–$C_6$)alkylamino, nitro, $C_1$–$C_6$ alkoxy, and $C_1$–$C_6$ alkyl. More preferred $R_1$ groups in Formula IIa are halogen, methyl, hydroxy, and methoxy; particularly preferred are fluoro and chloro.

Preferred compounds of Formula IIa include compounds of Formula IIb:

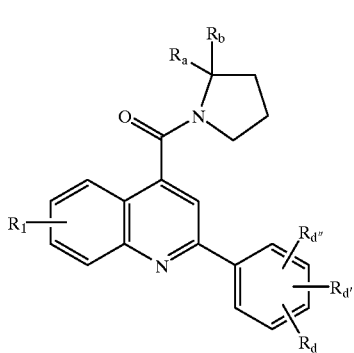

Formula IIb wherein $R_1$, $R_a$, and $R_b$, are defined as for Formula I and $R_d$, $R_{d'}$, and $R_{d''}$ are independently selected from the group consisting of hydrogen, halogen, cyano, nitro, trifluoromethyl, trifluoromethoxy, hydroxy, amino, and $C_1$–$C_6$ alkyl substituted with 0–2 $R_6$, $C_1$–$C_6$ alkoxy substituted with 0–2 $R_6$, —NH($C_{1-6}$ alkyl) substituted with 0–2 $R_6$, —N($C_1$–$C_6$ alkyl) ($C_1$–$C_6$ alkyl) wherein each alkyl is independently substituted with 0–2 $R_6$, —$XR_7$, and Y;

X at each occurrence is independently selected from the group consisting of —$CH_2$—, —$CHR_8$—, —O—, —NH—, and —$NR_8$—;

$R_6$ at each occurrence is independently selected from the group consisting of halogen, hydroxy, $C_1$–$C_6$ alkyl, $C_1$–$C_6$ alkoxy, —NH($C_1$–$C_6$ alkyl), —N($C_1$–$C_6$ alkyl) ($C_1$–$C_6$ alkyl), —NH—($C_1$–$C_6$ alkyl-Y), —N($C_1$–$C_6$ alkyl)—($C_1$–$C_6$ alkyl-Y), —NH—($C_1$–$C_6$ alkyl—N ($C_1$–$C_6$ alkyl) ($C_1$–$C_6$ alkyl)), —N($C_1$–$C_6$ alkyl)—($C_1$–$C_6$ alkyl-N($C_1$–$C_6$ alkyl) ($C_1$–$C_6$ alkyl)), morpholinyl, pyrrolidinyl, piperidinyl, thiomorpholinyl, piperazinyl, homopiperazinyl, —$S(O)_m$($C_1$–$C_6$ alkyl), trifluoromethyl, trifluoromethoxy, —CO($C_1$–$C_6$ alkyl), —CONH ($C_1$–$C_6$ alkyl), CON($C_1$–$C_6$ alkyl) ($C_1$–$C_6$ alkyl), —$XR_7$, and Y; wherein m is 0, 1, or 2;

$R_7$ and $R_8$ at each occurrence are independently $C_1$–$C_8$ alkyl, wherein $R_7$ and $R_8$ are substituted with 0, 1, 2, 3, or 4 substituents selected from the group consisting of oxo, hydroxy, halogen, amino, cyano, nitro, trifluoromethyl, trifluoromethoxy, $C_1$–$C_6$ alkoxy, —NH($C_1$–$C_6$ alkyl), —N($C_1$–$C_6$ alkyl) ($C_1$–$C_6$ alkyl); and Y at each occurrence is independently selected from 5- to 8-membered carbocycles or heterocycles, saturated or unsaturated containing zero, one or two heteroatom(s) selected from N, O, and S, with the point of attachment being either carbon or nitrogen (where applicable), and which may be further substituted with one or more substituents selected from halogen, oxo, hydroxy, amino, nitro, cyano, $C_1$–$C_6$ alkyl, $C_1$–$C_6$ alkoxy, and mono- or di $C_1$–$C_6$ alkylamino.

Preferred $R_1$ groups in Formula IIb include hydrogen, halogen, cyano, trifluoromethyl, trifluoromethoxy, hydroxy, amino, mono- and di($C_1$–$C_6$)alkylamino, nitro, $C_1$–$C_6$ alkoxy, and $C_1$–$C_6$ alkyl. More preferred $R_1$ groups in Formula IIb are halogen, methyl, hydroxy, and methoxy; particularly preferred are fluoro and chloro.

Preferred compounds of Formula IIb include those where W is phenyl is substituted with $R_d$, $R_{d'}$, and $R_{d''}$, where one of $R_d$, $R_{d'}$, and $R_{d''}$ is hydrogen and the other two are are independently hydrogen, halogen, hydroxy, $C_1$–$C_6$ alkylamino($C_1$–$C_6$)alkoxy, $C_1$–$C_6$ or alkoxy.

Still other preferred compounds of Formula IIb include those where W is phenyl para substituted with $C_1$–$C_6$ alkylamino($C_1$–$C_6$)alkoxy. Another preferred group of compounds of Formula IIb are those where W is phenyl or thienyl, more preferably phenyl, each of which is optionally mono- of disubstituted with groups independently selected from $C_1$–$C_6$ alkyl, $C_1$–$C_6$ alkoxy, halogen, hydroxy, $C_1$–$C_6$ alkylamino($C_1$–$C_6$)alkoxy, and $C_1$–$C_6$ alkoxy. More preferably, the phenyl and thienyl groups are mono- or disubstituted with $C_1$–$C_2$ alkyl, $C_1$–$C_2$ alkoxy, halogen, preferably chloro or fluoro, hydroxy, mono- or di($C_1$–$C_2$) alkylamino($C_1$–$C_2$)alkoxy, and $C_1$–$C_6$ alkoxy.

More preferred W groups of Formula IIb include 4-halophenyl and 3,4-dihalophenyl, particularly, 4-fluoro and 4-chlorophenyl. Still other more preferred W groups in Formula IIb are 4-alkoxyphenyl groups, particularly 4-methoxyphenyl. Other more preferred W groups in Formula IIb are 2-($C_1$–$C_6$)alkylphenyl such as 2-methyl and 2-ethylphenyl, haloalkoxyphenyl such as 3-bromopropoxyphenyl, 3-alkoxyphenyl such as 3-methoxyphenyl, and 2-halophenyl, particularly 2-fluoro and 2-chlorophenyl. Still other more preferred w groups include 3,4-dihalophenyl groups, particularly where the halogens are fluoro or chloro. Other more prefered W groups are 2-halo-4-hydroxyphenyl and 2-halo-4-alkoxyphenyl groups, particularly 2-fluoro and 2-chloro-4-hydroxyphenyl and 2-fluoro-4-methoxy- or ethoxyphenyl.

Yet other preferred compounds of Formula IIb include those where $R_b$ is hydrogen or $C_1$–$C_2$ alkyl and $R_a$ is hydroxy ($C_1$–$C_6$) alkyl, 4-($C_1$–$C_6$)alkyl-[1,4]diazepan-1-yl ($C_1$–$C_6$)alkyl, 4-($C_1$–$C_6$)alkyl-piperazin-1-yl($C_1$–$C_6$)alkyl, mono- or di ($C_1$–$C_6$) alkylamino ($C_1$–$C_6$) alkyl (($C_1$–$C_6$) alkyl) amino ($C_1$–$C_6$) alkyl, mono- or di($C_1$–$C_6$)alkylamino ($C_1$–$C_6$)alkylamino($C_1$–$C_6$)alkyl, or pyrrolidin-1-yl or piperidin-1-yl ($C_1$–$C_6$)alkylamino($C_1$–$C_6$)alkyl. Among these $R_a$ groups, those that are more preferred include hydroxy($C_1$–$C_6$)methyl, 4-($C_1$–$C_2$)alkyl-[1,4]diazepan-1-ylmethyl, 4-($C_1$–$C_2$)alkyl-piperazin-1-ylmethyl, di ($C_1$–$C_3$) alkylamino ($C_2$–$C_4$) alkyl (($C_1$–$C_2$)alkyl)aminomethyl, di ($C_1$–$C_3$) alkylamino ($C_2$–$C_4$) alkylaminomethyl, or pyrrolidin-1-yl or piperidin-1-yl($C_2$–$C_3$)alkylaminomethyl. Particularly preferred $R_a$ groups are hydroxy($C_1$–$C_6$)methyl, 4-methyl-[1,4]diazepan-1-ylmethyl, 4-methylpiperazin-1-ylmethyl, 2-(dimethyl- and diethylamino)ethyl($C_1$–$C_2$ alkyl)aminomethyl, 2-(dimethyl- and diethylamino)ethylaminomethyl, or 2-(pyrrolidin-1-yl and piperidin-1-ylethyl)aminomethyl. Particularly preferred $R_b$ groups of Formula IIb are hydrogen.

Other preferred compounds of Formula II are compounds of Formula IIc:

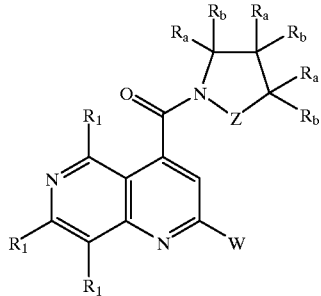

Formula IIc and the pharmaceutically acceptable salts thereof wherein $R_1$, $R_a$, $R_b$, W, and Z are defined as for Formula I.

Particular compounds of Formula IIc include compounds where W is phenyl, substituted with $R_d$, $R_{d'}$ and $R_{d''}$ which are independently selected from the group consisting of hydrogen, halogen, cyano, nitro, trifluoromethyl, trifluoromethoxy, hydroxy, amino, and $C_1$–$C_6$ alkyl substituted with 0–2 $R_6$, $C_1$–$C_6$ alkoxy substituted with 0–2 $R_6$, —NH($C_{1-6}$ alkyl) substituted with 0–2 $R_6$, —N($C_1$–$C_6$ alkyl) ($C_1$–$C_6$ alkyl) wherein each alkyl is independently substituted with 0–2 $R_6$, —$XR_7$, and Y;

X at each occurrence is independently selected from the group consisting of —$CH_2$—, —$CHR_8$—, —O—, —NH—, and —$NR_8$—;

$R_6$ at each occurrence is independently selected from the group consisting of halogen, hydroxy, $C_1$–$C_6$ alkyl, $C_1$–$C_6$ alkoxy, —NH($C_1$–$C_6$ alkyl), —N($C_1$–$C_6$ alkyl) ($C_1$–$C_6$ alkyl), —NH—($C_1$–$C_6$ alkyl-Y), —N($C_1$–$C_6$ alkyl)—($C_1$–$C_6$ alkyl-Y), —NH—($C_1$–$C_6$ alkyl—N($C_1$–$C_6$ alkyl) ($C_1$–$C_6$ alkyl)), —N($C_1$–$C_6$ alkyl)—($C_1$–$C_6$ alkyl-N($C_1$–$C_6$ alkyl) ($C_1$–$C_6$ alkyl)), morpholinyl, pyrrolidinyl, piperidinyl, thiomorpholinyl, piperazinyl, homopiperazinyl, —S(O)$_m$($C_1$–$C_6$ alkyl), trifluoromethyl, trifluoromethoxy, —CO($C_1$–$C_6$ alkyl), —CONH ($C_1$–$C_6$ alkyl), CON ($C_1$–$C_6$ alkyl) ($C_1$–$C_6$ alkyl), —$XR_7$, and Y; wherein m is 0, 1, or 2;

$R_7$ and $R_8$ at each occurrence independently carry the same definition as $R_2$, wherein $R_7$ and $R_8$ are substituted with 0, 1, 2, 3, or 4 substituents selected from the group consisting of oxo, hydroxy, halogen, amino, cyano, nitro, trifluoromethyl, trifluoromethoxy, $C_1$–$C_6$ alkoxy, —NH($C_1$–$C_6$ alkyl), —N($C_1$–$C_6$ alkyl) ($C_1$–$C_6$ alkyl); and Y at each occurrence is independently selected from 5- to 8-membered carbocycles or heterocycles, saturated or unsaturated containing zero, one or two heteroatom(s) selected from N, O, and S, with the point of attachment being either carbon or nitrogen (where applicable), and which may be further substituted with one or more substituents selected from halogen, oxo, hydroxy, amino, nitro, cyano, $C_1$–$C_6$ alkyl, $C_1$–$C_6$ alkoxy, and mono- or di $C_1$–$C_6$ alkylamino.

Preferred compounds of Formula IIc include those where W is phenyl is substituted with $R_d$, $R_{d'}$, and $R_{d''}$, where one of $R_d$, $R_{d'}$, and $R_{d''}$ is hydrogen and the other two are are independently hydrogen, halogen, hydroxy, $C_1$–$C_6$ alkylamino($C_1$–$C_6$)alkoxy, $C_1$–$C_6$ or alkoxy.

Still other preferred compounds of Formula IIc include those where W is phenyl para substituted with $C_1$–$C_6$ alkylamino($C_1$–$C_6$)alkoxy. Another preferred group of compounds of Formula IIc are those where W is phenyl or thienyl, more preferably phenyl, each of which is optionally mono- of disubstituted with groups independently selected from $C_1$–$C_6$ alkyl, $C_1$–$C_6$ alkoxy, halogen, hydroxy, $C_1$–$C_6$ alkylamino($C_1$–$C_6$)alkoxy, and $C_1$–$C_6$ alkoxy. More preferably, the phenyl and thienyl groups are mono- or disubstituted with $C_1$–$C_2$ alkyl, $C_1$–$C_2$ alkoxy, halogen, preferably chloro or fluoro, hydroxy, mono- or di($C_1$–$C_2$) alkylamino($C_1$–$C_2$)alkoxy, and $C_1$–$C_6$ alkoxy.

More preferred W groups of Formula IIc include 4-halophenyl and 3,4-dihalophenyl, particularly, 4-fluoro and 4-chlorophenyl. Still other more preferred W groups in Formula IIc are 4-alkoxyphenyl groups, particularly 4-methoxyphenyl. Other more preferred W groups in Formula IIc are 2-($C_1$–$C_6$)alkylphenyl such as 2-methyl and 2-ethylphenyl, haloalkoxyphenyl such as 3-bromopropoxyphenyl, 3-alkoxyphenyl such as 3-methoxyphenyl, and 2-halophenyl, particularly 2-fluoro and 2-chlorophenyl. Still other more preferred W groups include 3,4-dihalophenyl groups, particularly where the halogens are fluoro or chloro. Other more prefered W groups are 2-halo-4-hydroxyphenyl and 2-halo-4-alkoxyphenyl groups, particularly 2-fluoro and 2-chloro-4-hydroxyphenyl and 2-fluoro-4-methoxy- or ethoxyphenyl.

Yet other preferred compounds of Formula IIc include those where $R_b$ is hydrogen or $C_1$–$C_2$ alkyl and $R_a$ is hydroxy($C_1$–$C_6$) alkyl, 4-($C_1$–$C_6$) alkyl-[1,4]diazepan-1-yl ($C_1$–$C_6$)alkyl, 4-($C_1$–$C_6$)alkyl-piperazin-1-yl($C_1$–$C_6$)alkyl, mono- or di($C_1$–$C_6$)alkylamino($C_1$–$C_6$)alkyl(($C_1$–$C_6$) alkyl) amino($C_1$–$C_6$)alkyl, mono- or di($C_1$–$C_6$)alkylamino($C_1$–$C_6$)alkylamino($C_1$–$C_6$)alkyl, or pyrrolidin-1-yl or piperidin-1-yl($C_1$–$C_6$)alkylamino($C_1$–$C_6$)alkyl. Among these $R_a$ groups, those that are more preferred include hydroxy($C_1$–$C_6$) methyl, 4-($C_1$–$C_2$)alkyl-[1,4]diazepan-1-ylmethyl, 4-($C_1$–$C_2$) alkyl-piperazin-1-ylmethyl, di ($C_1$–$C_3$)alkylamino ($C_2$–$C_4$)alkyl(($C_1$–$C_2$)alkyl)aminomethyl, di($C_1$–$C_3$) alkylamino($C_2$–$C_4$)alkylaminomethyl, or pyrrolidin-1-yl or piperidin-1-yl($C_2$–$C_3$)alkylaminomethyl. Particularly preferred $R_a$ groups are hydroxy($C_1$–$C_6$)methyl, 4-methyl-[1,4]diazepan-1-ylmethyl, 4-methylpiperazin-1-ylmethyl, 2-(dimethyl- and diethylamino)ethyl($C_1$–$C_2$ alkyl) aminomethyl, 2-(dimethyl- and diethylamino) ethylaminomethyl, or 2-(pyrrolidin-1-yl and piperidin-1-ylethyl)aminomethyl. Particularly preferred $R_b$ groups of Formula IIc are hydrogen.

Still other preferred compounds of Formula II are compounds of Formula IId,:

Formula IId

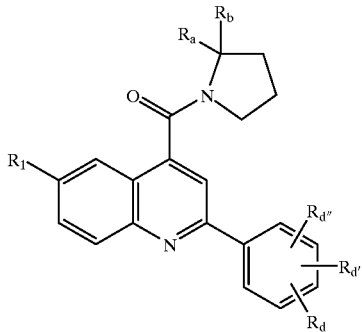

Formula IIE

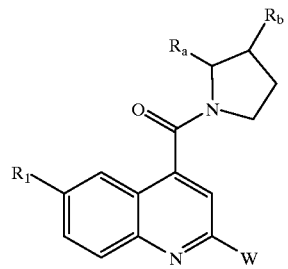

wherein $R_1$, $R_a$, and $R_b$, are defined as for Formula I and $R_d$, $R_{d'}$ and $R_{d''}$ are independently selected from the group consisting of hydrogen, halogen, cyano, nitro, trifluoromethyl, trifluoromethoxy, hydroxy, amino, and $C_1$–$C_6$ alkyl substituted with 0–2 $R_6$, $C_1$–$C_6$ alkoxy substituted with 0–2 $R_6$, —NH($C_{1-6}$ alkyl) substituted with 0–2 $R_6$, —N($C_1$–$C_6$ alkyl) ($C_1$–$C_6$ alkyl) wherein each alkyl is independently substituted with 0–2 $R_6$, —XR$_7$, and Y;

X at each occurrence is independently selected from the group consisting of —CH$_2$—, —CHR$_8$—, —O—, —NH—, and —NR$_8$—;

$R_6$ at each occurrence is independently selected from the group consisting of halogen, hydroxy, $C_1$–$C_6$ alkyl, $C_1$–$C_6$ alkoxy, —NH($C_1$–$C_6$ alkyl), —N($C_1$–$C_6$ alkyl) ($C_1$–$C_6$ alkyl), —NH—($C_1$–$C_6$ alkyl-Y), —N($C_1$–$C_6$ alkyl)—($C_1$–$C_6$ alkyl-Y), —NH—($C_1$–$C_6$ alkyl—N ($C_1$–$C_6$ alkyl) ($C_1$–$C_6$ alkyl)), —N($C_1$–$C_6$ alkyl)—($C_1$–$C_6$ alkyl-N($C_1$–$C_6$ alkyl) ($C_1$–$C_6$ alkyl)), morpholinyl, pyrrolidinyl, piperidinyl, thiomorpholinyl, piperazinyl, homopiperazinyl, —S(O)$_m$($C_1$–$C_6$ alkyl), trifluoromethyl, trifluoromethoxy, —CO($C_1$–$C_6$ alkyl), —CONH ($C_1$–$C_6$ alkyl), CON($C_1$–$C_6$ alkyl) ($C_1$–$C_6$ alkyl), —XR$_7$, and Y; wherein m is 0, 1, or 2;

$R_7$ and $R_8$ at each occurrence are independently $C_1$–$C_8$ alkyl, wherein $R_7$ and $R_8$ are substituted with 0, 1, 2, 3, or 4 substituents selected from the group consisting of oxo, hydroxy, halogen, amino, cyano, nitro, trifluoromethyl, trifluoromethoxy, $C_1$–$C_6$ alkoxy, —NH($C_1$–$C_6$ alkyl), —N($C_1$–$C_6$ alkyl) ($C_1$–$C_6$ alkyl); and Y at each occurrence is independently selected from 5- to 8-membered carbocycles or heterocycles, saturated or unsaturated containing zero, one or two heteroatom(s) selected from N, O, and S, with the point of attachment being either carbon or nitrogen (where applicable), and which may be further substituted with one or more substituents selected from halogen, oxo, hydroxy, amino, nitro, cyano, $C_1$–$C_6$ alkyl, $C_1$–$C_6$ alkoxy, and mono- or di $C_1$–$C_6$ alkylamino.

Still other preferred compounds of Formula II are compounds of Formula IIE,:

and the pharmaceutically acceptable salts thereof; wherein $R_1$ is hydrogen, halogen, $C_1$–$C_2$alkyl or $C_1$–$C_2$alkoxy;

$R_a$ is selected from hydrogen, halogen, $C_1$–$C_6$ alkyl, $C_1$–$C_6$alkoxy, haloalkyl, haloalkoxy, hydroxy $C_1$–$C_6$alkyl, mono- or di-($C_1$–$C_6$)alkylamino, mono- or di-($C_1$–$C_6$) alkyl$_3$amino($C_1$–$C_6$)alkyl where each alkyl$_3$ may be substituted by mono- or di-($C_1$–$C_6$) alkylamino, heterocycloalkyl($C_1$–$C_6$)alkyl, heterocycloalkyl($C_1$–$C_6$)alkylamino, and heterocycloalkyl which may be substituted by $C_1$–$C_6$alkyl;

$R_b$ is selected from hydrogen, halogen, hydroxy, methyl, and ethyl,; and

W is phenyl, pyridyl, thienyl, or pyrimidinyl, each of which is substituted with $R_d$, $R_{d'}$, and $R_{d''}$ where $R_d$, $R_{d'}$, and $R_{d''}$ are independently selected from hydrogen, halogen, hydroxy, haloalkyl, haloalkoxy $C_1$–$C_6$ alkyl, $C_1$–$C_6$ alkoxy, mono- or di-($C_1$–$C_6$)alkylamino, di($C_1$–$C_6$) alkylamino($C_1$–$C_6$)alkoxy, $C_3$–$C_7$ cycloalkylamino ($C_1$–$C_6$) alkoxy, and heteroaryl ($C_1$–$C_6$) alkoxy.

Preferred compounds of Formula IIE include those where $R_b$ is hydrogen; one of $R_d$, $R_{d'}$, and $R_{d''}$ is hydrogen and the other two are independently selected from hydrogen, chloro, fluoro, hydroxy, methoxy, ethoxy, and methyl, ethyl, and $C_1$–$C_3$ alkylamino($C_1$–$C_2$)alkoxy. Other preferred compounds of Formula IIE are those where $R_b$ is hydrogen; $R_a$ is hydrogen or hydroxy($C_1$–$C_3$) alkyl, [(2-diethylamino-ethyl)-methyl-amino]methyl, or [(2-Diethylamino-ethyl)-methyl-amino]methyl. More preferred compounds of Formula IIE are those where $R_a$ is hydroxymethyl or hydrogen, particularly hydroxymethyl.

Preferred compounds of formula IIE include those where $R_1$ is hydrogen, halogen, $C_1$–$C_2$alkyl or $C_1$–$C_2$alkoxy;

$R_a$ is selected from hydrogen, halogen, $C_1$–$C_6$ alkyl, $C_1$–$C_6$alkoxy, haloalkyl, haloalkoxy, hydroxy $C_1$–$C_6$alkyl, mono- or di-($C_1$–$C_6$)alkylamino, mono- or di-($C_1$–$C_6$) alkyl$_3$amino($C_1$–$C_6$)alkyl where each alkyl$_3$ may be substituted by mono- or di-($C_1$–$C_6$) alkylamino, and ($C_1$–$C_6$) alkylamino;

$R_b$ is selected from hydrogen, halogen, hydroxy, methyl, and ethyl, and

W is phenyl, pyridyl, thienyl, or pyrimidinyl, each of which is substituted with $R_d$, $R_{d'}$, and $R_{d''}$, where $R_d$, $R_{d'}$, and $R_{d''}$ are independently selected from hydrogen, halogen, hydroxy, haloalkyl, haloalkoxy di($C_1$–$C_6$) alkylamino($C_1$–$C_6$)alkoxy, $C_1$–$C_6$ alkyl, $C_1$–$C_6$ alkoxy, mono- or di-($C_1$–$C_6$) alkylamino, $C_1$–$C_6$ alkylamino ($C_1$–$C_6$)alkoxy, and $C_3$–$C_7$ cycloalkylamino ($C_1$–$C_6$) alkoxy.

Other preferred compounds of Formula IIE are those where $R_b$ is hydrogen. More preferred compounds of Formula IIE are those where $R_d$, $R_{d'}$, and $R_{d''}$ are independently hydrogen, fluorine or hydroxyl. Still other more preferred compounds of Formula IIE are those where W is phenyl carrying $R_d$, $R_{d'}$, and $R_{d''}$ where one of $R_d$, $R_{d'}$, and $R_{d''}$ is hydrogen and the other two are independently hydrogen, $C_1$–$C_6$ alkyl, $C_1$–$C_6$ alkoxy, mono- or di-($C_1$–$C_6$) alkylamino, $C_1$–$C_6$ alkylamino($C_1$–$C_6$)alkoxy, or $C_3$–$C_7$ cycloalkylamino($C_1$–$C_6$) alkoxy.

Particularly preferred compounds of Formula IIE are those where $R_b$ is hydrogen and $R_a$ is hydrogen, hydroxy ($C_1$–$C_6$)alkyl, 4-($C_1$–$C_6$)alkyl-[1,4]diazepan-1-yl($C_1$–$C_6$) alkyl, 4-($C_1$–$C_6$)alkyl-piperazin-1-yl($C_1$–$C_6$)alkyl, mono- or di ($C_1$–$C_6$)alkylamino($C_1$–$C_6$)alkyl(($C_1$–$C_6$) alkyl)amino ($C_1$–$C_6$)alkyl, mono- or di($C_1$–$C_6$)alkylamino($C_1$–$C_6$) alkylamino($C_1$–$C_6$)alkyl, or pyrrolidin-1-yl or piperidin-1-yl ($C_1$–$C_6$)alkylamino($C_1$–$C_6$)alkyl.

Still other particularly preferred compounds of Formula IIE are those where $R_b$ is hydrogen and $R_a$ is hydrogen, hydroxymethyl, [(2-diethylamino-ethyl)-methyl-amino] methyl, or [(2-Diethylamino-ethyl)-methyl-amino]methyl. Yet other particularly preferred compounds of Formula IIE are those where W is phenyl carrying $R_d$, $R_{d'}$, and $R_{d''}$ where one of $R_d$, $R_{d'}$, and $R_{d''}$ is hydrogen and the other two are independently hydrogen, halogen, hydroxy, $C_1$–$C_6$ alkylamino($C_1$–$C_6$)alkoxy, $C_1$–$C_6$ or alkoxy.

Other preferred compounds of the invention are compounds of Formula III:

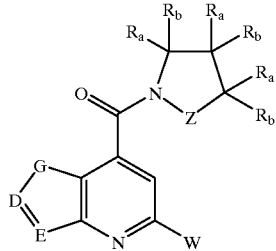

Formula III and the pharmaceutically acceptable salts thereof, wherein G, D, E, $R_a$, $R_b$, W, and Z are defined as for Formula I.

Compounds of Formula III also include compounds of Formula IIIa:

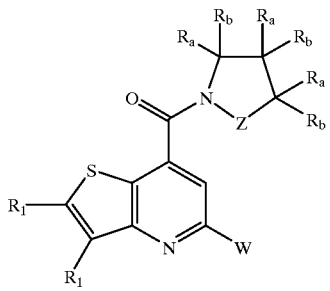

Formula IIIa and the pharmaceutically acceptable salts thereof, wherein $R_1$, $R_a$, $R_b$, W, and Z are defined as for Formula IIb.

Particular compounds of Formula IIIa include compounds where W is phenyl, substituted with $R_d$, $R_{d'}$, and $R_{d''}$ (defined as for Formula IIb).

Still other preferred compounds of the invention are compounds of formula IV:

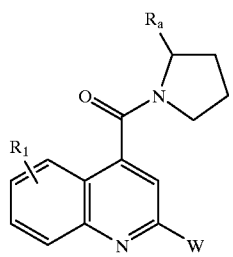

Formula IV wherein $R_a$ and W are defined as in Formula I; and
$R_1$ is selected from the group consisting of hydrogen, halogen, hydroxy, $C_1$–$C_8$ alkoxy, and $C_1$–$C_6$ alkyl.

Other preferred compounds of formula IV include those where
W is defined as in formula I; $R_1$ is selected from the group consisting of hydrogen, halogen, hydroxy, $C_1$–$C_8$ alkoxy, and $C_1$–$C_6$ alkyl;
$R_a$ is selected from the group consisting of hydrogen, —$XR_7$, and $C_1$–$C_6$ alkyl, wherein the $C_1$–$C_6$ alkyl is optionally substituted with 0, 1, or 2 $R_6$;
$R_6$ is selected from the group consisting of —NH— ($C_1$–$C_6$ alkyl-Y), —N($C_1$–$C_6$ alkyl)—($C_1$–$C_6$ alkyl-Y), —NH—($C_1$–$C_6$ alkyl—N($C_1$–$C_6$ alkyl) ($C_1$–$C_6$ alkyl)), and —N($C_1$–$C_6$ alkyl)—($C_1$–$C_6$ alkyl—N ($C_1$–$C_6$ alkyl) ($C_1$–$C_6$ alkyl));
X is selected from the group consisting of —$CH_2$—, —$CHR_8$—, —C(O)—, —C(O)O—, —C(O)NH—, —C(O)N($C_1$–$C_6$ alkyl)—, and —C(O)N($C_1$–$C_6$ alkyl) ($C_1$–$C_6$ alkyl)—;
$R_7$ and $R_8$ at each occurrence are independently $C_1$–$C_6$ alkyl optionally substituted with 1, 2, 3, or 4 substituents selected from the group consisting of hydroxy, amino, —NH($C_1$–$C_8$ alkyl), —NH ($C_1$–$C_8$ alkyl) ($C_1$–$C_8$ alkyl); and
Y is selected from 5- to 8-membered carbocycles or heterocycles, which are saturated or unsaturated and contain zero, one or two heteroatoms selected from N, O, and S, with the point of attachment being either carbon or nitrogen (where applicable), and which may be further substituted with 1, 2, 3, or 4 substituents selected from the group consisting of halogen, oxo, hydroxy, amino, nitro, cyano, alkyl, $C_1$–$C_6$ alkoxy, —NH($C_1$–$C_6$ alkyl), —N($C_1$–$C_6$ alkyl) ( $C_1$–$C_6$ alkyl), and —$S(O)_a$($C_1$–$C_6$ alkyl); wherein
a is 0, 1, or 2.

Yet other preferred compounds of formula IV include those where: $R_1$ is selected from the group consisting of hydrogen, halogen, hydroxy, $C_1$–$C_8$ alkoxy, and $C_1$–$C_6$ alkyl;
$R_a$ is selected from the group consisting of hydrogen, —$XR_7$, and $C_1$–$C_6$ alkyl, wherein the $C_1$–$C_6$ alkyl is optionally substituted with 0, 1, or 2 $R_6$;
$R_6$ is selected from the group consisting of —NH— ($C_1$–$C_6$ alkyl-Y), —N($C_1$–$C_6$ alkyl)—($C_1$–$C_6$ alkyl-Y), —NH—($C_1$–$C_6$ alkyl—N($C_1$–$C_6$ alkyl) ($C_1$–$C_6$ alkyl)), and —N($C_1$–$C_6$ alkyl)—($C_1$–$C_6$ alkyl—N ($C_1$–$C_6$ alkyl) ($C_1$–$C_6$ alkyl));
X is selected from the group consisting of —$CH_2$—, —$CHR_8$—, —C(O)—, —C(O)O—, —C(O)NH—, —C(O)N($C_1$–$C_6$ alkyl)—, and —C(O)N($C_1$–$C_6$ alkyl) ($C_1$–$C_6$ alkyl)—; and $R_7$ and $R_8$ at each occurrence are independently $C_1$–$C_6$ alkyl optionally substituted with 1, 2, 3, or 4 substituents selected from the group consisting of hydroxy, amino, —NH($C_1$–$C_8$ alkyl), —NH($C_1$–$C_8$ alkyl) ($C_1$–$C_8$ alkyl);

W is thiophene or phenyl, wherein each is unsubstituted or substituted with 1, 2, or 3 substituents selected from the group consisting of halogen, hydroxy, $C_1$–$C_6$ alkoxy, optionally substituted with amino, NH($C_1$–$C_6$ alkyl), NH($C_3$–$C_6$ cycloalkyl), halogen, and Y; and Y is selected from 5- to 8-membered carbocycles or heterocycles, which are saturated or unsaturated and contain zero, one or two heteroatoms selected from N, O, and S, with the point of attachment being either carbon or nitrogen (where applicable), and which may be further substituted with 1, 2, 3, or 4 substituents selected from the group consisting of halogen, oxo, hydroxy, amino, nitro, cyano, $C_1$–$C_6$ alkyl, $C_1$–$C_6$ alkoxy, —NH($C_1$–$C_6$ alkyl), —N($C_1$–$C_6$ alkyl) ($C_1$–$C_6$ alkyl), and —S(O)$_a$($C_1$–$C_6$ alkyl); wherein a is 0, 1, or 2.

In other preferred compounds of Formula IV, $R_a$ is selected from hydrogen, halogen, $C_1$–$C_6$ alkyl, $C_1$–$C_6$alkoxy, haloalkyl, haloalkoxy, hydroxy $C_1$–$C_6$alkyl, mono- or di-($C_1$–$C_6$)alkylamino, mono- or di-($C_1$–$C_6$) alkyl$_3$amino($C_1$–$C_6$)alkyl where each alkyl$_3$ may be substituted by mono- or di($C_1$–$C_6$) alkylamino, heterocycloalkyl ($C_1$–$C_6$)alkyl, heterocycloalkyl($C_1$–$C_6$)alkylamino, and heterocycloalkyl which may be substituted by $C_1$–$C_6$alkyl;

$R_b$ is selected from hydrogen, halogen, hydroxy, methyl, and ethyl, and

W is phenyl, pyridyl, thienyl, or pyrimidinyl, each of which is substituted with $R_d$, $R_{d'}$, and $R_{d''}$, where $R_d$, $R_{d'}$, and $R_{d''}$ are independently selected from hydrogen, halogen, hydroxy, haloalkyl, haloalkoxy di($C_1$–$C_6$) alkylamino($C_1$–$C_6$)alkoxy, $C_1$–$C_6$ alkyl, $C_1$–$C_6$ alkoxy, mono- or di-($C_1$–$C_6$)alkylamino, $C_1$–$C_6$ alkylamino ($C_1$–$C_6$)alkoxy, $C_3$–$C_7$ cycloalkylamino($C_1$–$C_6$) alkoxy, and heteroaryl($C_1$–$C_6$)alkoxy.

More preferred compounds of Formula IV are those where $R_d$, $R_{d'}$, and Rd are independently hydrogen, fluorine or hydroxyl. Still other more preferred compounds of Formula IV are those where W is phenyl carrying $R_d$, $R_{d'}$, and $R_{d''}$ where one of $R_d$, $R_{d'}$, and $R_{d''}$ is hydrogen and the other two are independently hydrogen, haloalkyl, haloalkoxy $C_1$–$C_6$ alkyl, $C_1$–$C_6$ alkoxy, mono- or di-($C_1$–$C_6$) alkylamino, $C_1$–$C_6$ alkylamino($C_1$–$C_6$)alkoxy, $C_3$–$C_7$ cycloalkylamino($C_1$–$C_6$) alkoxy, or heteroaryl ($C_1$–$C_6$) alkoxy.

Particularly preferred compounds of Formula IV are those where $R_b$ is hydrogen and $R_a$ is hydrogen, hydroxy($C_1$–$C_6$) alkyl, 4-($C_1$–$C_6$)alkyl-[1,4]diazepan-1-yl ($C_1$–$C_6$) alkyl, 4 -($C_1$–$C_6$)alkyl-piperazin-1-yl ($C_1$–$C_6$)alkyl, mono- or di ($C_1$–$C_6$)alkylamino($C_1$–$C_6$)alkyl(($C_1$–$C_6$)alkyl)amino ($C_1$–$C_6$)alkyl, mono- or di($C_1$–$C_6$)alkylamino($C_1$–$C_6$) alkylamino($C_1$–$C_6$)alkyl, or pyrrolidin-1-yl or piperidin-1-yl($C_1$–$C_6$)alkylamino($C_1$–$C_6$)alkyl.

Still other particularly preferred compounds of Formula IV are those where $R_b$ is hydrogen and $R_a$ is hydrogen, hydroxymethyl, [(2-diethylamino-ethyl)-methyl-amino] methyl, or [(2-Diethylamino-ethyl)-methyl-amino]methyl. Yet other particularly preferred compounds of Formula IV are those where W is phenyl carrying $R_d$, $R_{d'}$, and $R_{d''}$ where one of $R_d$, $R_{d'}$, and $R_{d''}$ is hydrogen and the other two are independently hydrogen, halogen, hydroxy, $C_1$–$C_6$ alkylamino($C_1$–$C_6$)alkoxy, $C_1$–$C_6$ or alkoxy.

In a preferred aspect, this invention provides quinolines that are substituted at the 2-position by a carbocyclic or heterocyclic group (such as optionally substituted phenyl or optionally substituted thienyl), at the 4-position by a pyrrolidinyl carbonyl group, and at the 6-position by a group $R_2$ (defined above for Formula I). The pyrrolidine of the pyrrolidinyl carbonyl group is either unsubstituted or substituted at the 2 and/or 3 position. Preferred substituents at the 2 position of this pyrrolidine include hydroxymethyl, and aminoalkyl groups such as 2 -ethylamino-1-ethyl-1-methyl-aminomethyl, N-ethylpiperizine, 2-dimethylamino-1-ethyl-1-methyl-aminomethyl, (N-methylhomopiperizinyl)methyl, (N-methylpiperizinyl)methyl, N-piperidinylethylaminomethyl, and N-pyrrolidinylethylaminomethyl. Particularly preferred compounds having a substituent at the 2-position of the pyrrolidine group are those that are unsubstituted at the 3 -position. Preferred substituents at the 3-position of this pyrrolidine include hydroxy and halogen. Particularly preferred compounds having a substituent at the 3-position of the pyrrolidine group are those that are unsubstituted at the 2-position.

This invention relates to heterocyclic derivatives, in particular quinoline carbonyl pyrrolidines and more particularly, to such compounds that bind to the benzodiazepine site of $GABA_A$ receptors, including human $GABA_A$ receptors. This invention also includes such compounds that bind to the benzodiazepine site of $GABA_A$ receptors, including human $GABA_A$ receptors. Without wishing to be bound to any particular theory, it is believed that the interaction of the compounds of Formula I with the benzodiazepine site results in the pharmaceutical utility of these compounds.

The invention further comprises methods of treating patients in need of such treatment with a therapeutically effective amount of a compound of the invention sufficient to alter the symptoms of a CNS disorder. Compounds of the inventions that act as agonists at $\alpha_2\beta_2\gamma_2$ and $\alpha_2\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_2\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases, and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder ± agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

The invention also provides pharmaceutical compositions comprising compounds of the invention together with a pharmaceutically acceptable carrier. Such pharmaceutical compositions include packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5 -methylisoxazol-3-yl)-6-(1-methyl-1,2,3-triazol-4-yl) methyloxy-1,2,4-triazolo [3,4-a]phthalazine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3 -b]pyridazines, in combination with SSRIs.

The present invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 146. The $GABA_A$ receptors used to determine in vitro binding may be obtained from a variety of sources, for example from preparations of rat cortex or from cells expressing cloned human $GABA_A$ receptors.

The present invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given a therapeutically effective amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 147.

The $GABA_A$ receptor ligands provided by this invention and labeled derivatives thereof are also useful as standards and reagents in determining the ability of a potential pharmaceutical to bind to the $GABA_A$ receptor.

Labeled derivatives the $GABA_A$ receptor ligands provided by this invention are also useful as radiotracers for positron emission tomography (PET) imaging or for single photon emission computerized tomography (SPECT).

Definitions

If the compounds of the invention have asymmetric centers, then this invention includes all of the individual stereoisomers and mixtures thereof.

In addition, compounds with carbon—carbon double bonds may occur in cis, trans, Z- and E- forms, with all isomeric forms of the compounds being included in the invention.

When any variable (e.g. $C_{1-6}$ alkyl, $C_{1-8}$ alkyl, $R_1$–$R_8$, $R_a$, $R_b$, $R_d$, $R_{d'}$, $R_{d''}$, W, X, Y or Y') occurs more than one time in Formula I, Formula II, IIa, IIb, IIc, IId, Formula III, IIIa, or Formula IV or any substituent definition, its definition on each occurrence is independent of its definition at every other occurrence. Thus, where a substituent definition carries two identical groups, e.g., —N($R_2$)$_2$ or —N(alkyl) (alkyl), the definition of each $R_2$ or alkyl group is independent of the other.

As used herein, the term "alkenyl" refers to a straight or branched hydrocarbon of a designed number of carbon atoms containing at least one carbon—carbon double bond. Examples of "alkenyl" include vinyl, allyl, and 2-methyl-3-heptenyl.

The term "alkoxy" represents an alkyl group of indicated number of carbon atoms attached to the parent molecular moiety through an oxygen atom. Examples of alkoxy groups include methoxy, ethoxy, propoxy and isopropoxy.

As used herein, the term "alkyl" includes those alkyl groups of the designated number of carbon atoms. Alkyl groups may be straight or branched. Examples of "alkyl" include methyl, ethyl, propyl, isopropyl, butyl, iso-, sec- and tert-butyl, pentyl, hexyl, heptyl, 3-ethylbutyl, and the like. The terms $alkyl_1$ and $alkyl_2$ are used herein to designate alkyl groups that may be the same or different and have from 1–6 carbon atoms.

The term "alkynyl" refers to a straight or branched hydrocarbon of a designed number of carbon atoms containing at least one carbon—carbon triple bond. Examples of "alkynyl" include propargyl, propyne, and 3-hexynyl.

As used herein, "carbocyclic group" refers to aromatic carbocyclic ring systems and to cycloalkyl ring systems that have one or more double or triple bonds.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred examples of aryl groups include phenyl and naphthyl. The aryl groups herein are unsubstituted or, as specified, substituted in one or more substitutable positions with various groups. Thus, such aryl groups are optionally substituted with, for example, $C_1$–$C_6$ alkyl, $C_1$–$C_6$ alkoxy, halogen, hydroxy, cyano, nitro, amino, mono- or di($C_1$–$C_6$) alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl. Preferred W aryl groups are optionally substituted phenyl groups, where the substituents are as specified elsewhere herein. The term "cycloalkenyl" refers to a $C_3$–$C_8$ cyclic hydrocarbon containing at least one carbon—carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" refers to a $C_3$–$C_8$ cyclic hydrocarbon. Examples of cycloalkyl include cyclopropyl, cyclobutyl, cyclopentyl, cyclohexyl, cycloheptyl and cyclooctyl.

The term "cycloalkynyl" refers to a $C_5$–$C_{10}$ cyclic hydrocarbon containing at least one carbon—carbon triple bond. Examples of cycloalkynyl include cyclohexynyl, cycloheptynyl and cyclodecynyl.

The term "halogen" indicates fluorine, chlorine, bromine, and iodine.

"Haloalkyl" refers to branched and straight-chain saturated aliphatic hydrocarbon groups having the specified number of carbon atoms and substituted with 1 or more halogen atoms. Examples of haloalkyl include, but are not limited to, mono-, di-, or trifluoromethyl, mono-, di-, or trichloromethyl, mono-, di-, tri-, tetra-, or pentafluoroethyl, 3-bromopropyl, and mono-, di-, tri-, tetra-, or pentachloroethyl. Typical haloalkyl groups will have 1 to about 8 carbon atoms, more typically 1 to about 6 carbon atoms. Preferred haloalkyl groups are trifluoromethyl and 2,2-difluoroethyl.

"Halolkoxy" represents a haloalkyl group as defined above with the indicated number of carbon atoms attached through an oxygen bridge. Preferred haloalkoxy groups are halo($C_1$–$C_6$)alkoxy groups. Examples of haloalkoxy groups are trifluoromethoxy, 2,2-difluoroethoxy, 2,2,3-trifluoropropoxy and perfluoroisopropoxy.

As used herein, the terms "heterocyclic group" or "heterocycloalkyl" are intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 hetero atoms independently selected from N, O and S and including any bicyclic group in which any of the above-defined heterocyclic rings is fused to a benzene ring. The nitrogen and sulfur hetero atoms may optionally be oxidized. The term "heteroaryl" is used to specifically indicate aromatic heterocyclic groups.

The heterocyclic ring may be attached to its pendant group at any hetero atom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and 0 atoms in the heterocycle exceeds 1, then these hetero atoms are not adjacent to one another. It is preferred that the total number of S and 0 atoms in the heterocycle is not more than 1. As used herein, the term "aromatic heterocyclic system" is intended to mean a stable 5-to 7-membered monocyclic or bicyclic or 7- to 10 -membered bicyclic heterocyclic aromatic ring which consists of carbon atoms and from 1 to 4 hetero atoms independently selected from nitrogen, oxygen and sulfur. It is preferred that the total number of sulfur and oxygen atoms in the aromatic heterocycle is not more than 1.

Examples of heterocycles include, but are not limited to, acridinyl, azocinyl, benzimidazolyl, benzofuranyl, benzothio-furanyl, benzothiophenyl, benzoxazolyl, benzothiazolyl, benzotriazolyl, benoztetrazolyl, benzisoxazolyl, benzisothiazolyl, benzimidazolinyl, carbazolyl, NH—carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5 -oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3 -thiadiazolyl, 1,2,4-thiadiazolyl, 1,2,5-thiadiazolyl, 1,3,4 -thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. The heterocycles herein are unsubstituted or, as specified, substituted in one or more substitutable positions with various groups. Thus, such heterocycles are optionally substituted with, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono- or di($C_1$–$C_6$) alkylamino($C_1$–$C_6$)alkyl. Preferred W heterocycle groups are optionally substituted pyridyl, pyrimidinyl, and thienyl groups, more preferably pyridyl groups, where the substituents are as specified elsewhere herein.

The formula: "—$CH_2N(C_2H_5)CH_2CH_2N(C_2H_5)_2$" as used in e.g., Example no. 116, represents a [(2-diethylamino-ethyl)-ethyl-amino]methyl group. This group can be represented by the formula:

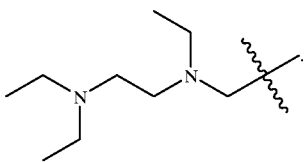

The formula: "—CH$_2$N(CH$_3$)CH$_2$CH$_2$N(C$_2$H$_5$)$_2$", as used, e.g., in Example no. 109, represents a [(2-diethylamino-ethyl)-methyl-amino]methyl group. This group can be represented by the formula:

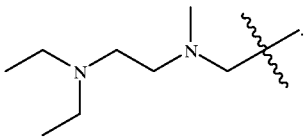

The formula: "—CH$_2$NCH$_2$CH$_2$N (C$_2$H$_5$)$_2$" represents a [2-(diethylamino)ethylamino]methyl group. This group can be represented by the formula:

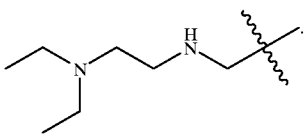

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The present invention also encompasses prodrugs of the compounds of Formula I.

The present invention also encompasses acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, a compound according to claim 1 or a pharmaceutically acceptable salt, with or without excipients, may be added to the animal's feed or drinking water. It may be convenient to formulate these animal feed and drinking water compositions so that the animal ingests a therapeutically effective quantity of the compound of formula I or a pharmaceutically acceptable salt thereof, in a meal or during the course of a day. It may also be convenient to present the compound of formula I or a pharmaceutically acceptable salt thereof, as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have pharmacological properties that include, but are not limited to, oral bioavailability, low toxicity, low serum protein binding and desirable in vitro and in vivo half-lives. Penetration of the blood brain barrier for compounds used to treat CNS disorders is generally necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

Preparation of Compounds

A general illustration of the preparation of compounds of Formula I in the present invention is given in Scheme I and Scheme II:

Scheme I

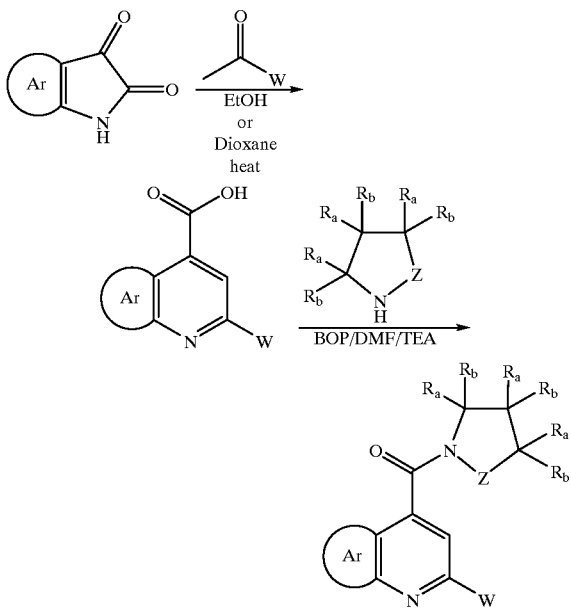

wherein the Ar ring, W, $R_a$, and $R_b$ are as defined above in formula I, and Z is $(CR_aR_b)_n$, wherein n is 1, 2, or 3.

In Scheme I BOP is benzotriazol-1-yloxytris (dimethylamino)-phosphoniumhexafluorophosphate, TEA is triethylamine, DMF is N,N-dimethylformamide, EtOH is ethanol, and dioxane is 1,4-dioxane. Heat, as used herein, means elevated temperature, such as 40 to 250° C. Those skilled in the art will recognize that it may be necessary to utilize different solvents or reagents to achieve some of the above transformations.

Scheme II

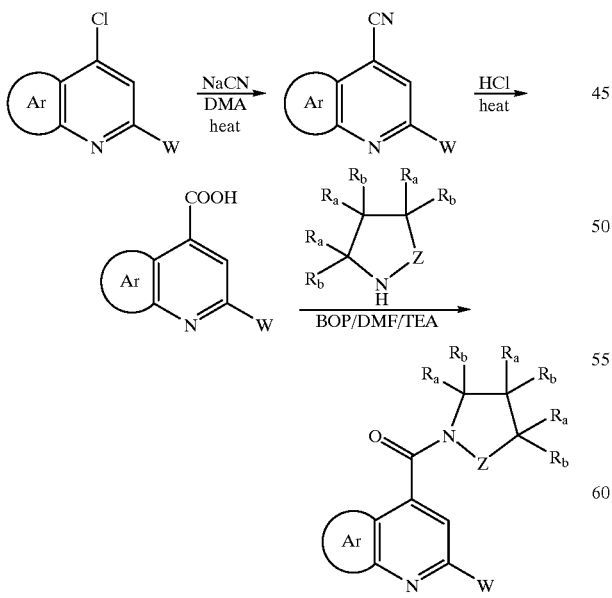

wherein the Ar ring, W, $R_a$, and $R_b$ are as defined above in formula I, and Z is $(CR_aR_b)_n$, wherein n is 1, 2, or 3.

In Scheme II, TEA is triethylamine, BOP is benzotriazol-1-yloxytris(dimethylamino)-phosphoniumhexafluorophosphate, HCl is concentrated (12M) hydrochloric acid, DMF is N,N-dimethylformamide, and DMA is N,N-dimethylacetamide. Heat, as used herein, means elevated temperature, such as 40 to 250° C. Those skilled in the art will recognize that it may be necessary to utilize different solvents or reagents to achieve some of the above transformations.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. Unless otherwise specified all reagents and solvent are of standard commercial grade and are used without further purification. In some cases, protection of reactive functionalities may be necessary to achieve some of the above transformations. In general, such need for protecting groups, as well as the conditions necessary to attach and remove such groups, will be apparent to those skilled in the art of organic synthesis.

EXAMPLES

Example 1

Preparation of (R)-1-[[2-(3,4-difluoroPhenyl)-4-quinoliny]carbonyl]-2-hydroxymethyl-pyrrolidine

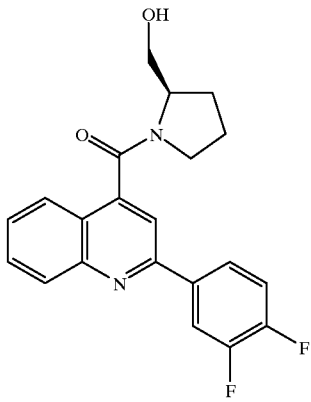

(1) 2-(3,4-difluoroPhenyl)-4-quinoline Carboxylic Acid

A mixture of 2,3-indolinedione (5 g, 0.03 mole), 3',4'-difluoroacetophenone (5 g, 0.03 mole) and potassium hydroxide (3 g, 0.05 mole) in 1,4-dioxane (50 mL) is heated at 105° C. for 48 hours. The reaction solution is then cooled to room temperature and concentrated under reduced pressure. The residue is treated with EtOAc and extracted with water. The pH of the aqueous layer is adjusted to 5–6 with 1N HCl, the resulting solid is collected by vacuum filtration, washed with water, and dried to give the titled compound (450 mg) as a yellow solid.

2) 2-(3,4-difluoroPhenyl)-4-quinoliny]carbonyl]-2-hydroxymethyl-pyrrolidine

A mixture of 2-(3,4-difluoroPhenyl)-4-quinoline carboxylic acid (100 mg), BOP (220 mg) and (R)-(−)-pyrrolidine methanol (0.1 mL) in 1 ml of DMF is stirred at room temperature for 18 hours. The mixture is added to saturated aqueous NaHCO₃ solution and extracted three times with EtOAc. The combined EtOAc layers are washed with brine and water, dried over $Na_2SO_4$, filtered and concentrated to afford a foam. The foam is purified by preparative silica gel thin layer chromatography, using 10% methanol in methylene chloride as the developing solvent. The desired product is obtained as a free base. $^1$H NMR ($CDCl_3$) d 1.77–1.87 (3H, m), 2.16–2.22 (1H, m), 3.18–3.26 (2H, m), 3.83–3.95 (2H, m), 4.52–4.56 (1H, m), 7.23–7.30 (1H, m), 7.57 (1H, m), 7.73–7.78 (2H, m), 7.83 (1H, d), 7.87 (1H, m), 8.03–8.10 (1H, m), 8.15 (1H, d). The hydrochloride salt was prepared by treating the free base in EtOAc with a solution of hydrogen chloride in ether and collecting the resulting solid by filtration.

LC-MS data: HPLC: 1.93 min (HPLC method: Zorbax XDB-$C_{18}$ column, 4.6×30 mm, 3.5 μm particle size, 3 min gradient from 0 to 100% B with 0.5 min hold at 100% B. Solvent A: 95% $H_2O$-5% MeOH-0.05% TFA; Solvent B: 95% MeOH-5% $H_2O$-0.05% TFA) MS ($ES^+$): m/e 356 $[M+H]^+$.

Examples 2–20

The following compounds are prepared by methods analogous to that of Example 1. These compounds have the structures shown below:

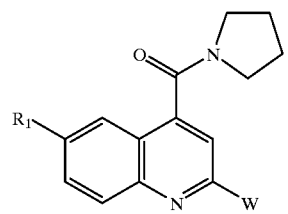

where $R_1$ and W are defined in the following Table 1. LC-MS data are given as HPLC retention times and $[M+H]^+$. The HPLC retention times shown in Table 1 were obtained by the method given in Example 1.

TABLE 1

| Example Number. | R1 | W | Compound Name | HPLC time (min) | $[M + H]^+$ |
|---|---|---|---|---|---|
| 2 | H | 2-fluoro-4-hydroxyphenyl | 1-[[2-(2-Fluoro-4-hydroxyphenyl)-4-quinolinyl]carbonyl]-pyrrolidine | 2.16 | 337.05 |
| 3 | F | 4-fluorophenyl | 1-[[6-Fluoro-2-(4-fluorophenyl)-4-quinolinyl]carbonyl]-pyrrolidine | 2.65 | 339.02 |
| 4 | F | 3,4-difluorophenyl | 1-[[6-Fluoro-2-(3,4-difluorophenyl)-4-quinolinyl]carbonyl]-pyrrolidine | 2.77 | 357.04 |
| 5 | H | 4-fluorophenyl | 1-[[2-(4-Fluorophenyl)-4-quinolinyl]carbonyl]-pyrrolidine | 2.49 | 321.05 |
| 6 | H | 2,4-difluorophenyl | 1-[[2-(2,4-Difluorophenyl)-4-quinolinyl]carbonyl]-pyrrolidine | 2.56 | 339.03 |

TABLE 1-continued

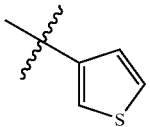

| Example Number. | R1 | W | Compound Name | HPLC time (min) | [M + H]+ |
|---|---|---|---|---|---|
| 7 | F | 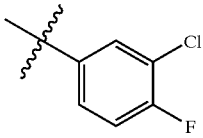 | 1-[[6-Fluoro-2-(3-thienyl)-4-quinolinyl]carbonyl]-pyrrolidine | 2.49 | 327.00 |
| 8 | H | 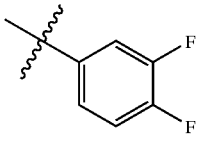 | 1-[[2-(3-Chloro-4-fluorophenyl)-4-quinolinyl]carbonyl]-pyrrolidine | 2.78 | 355.02 |
| 9 | H | 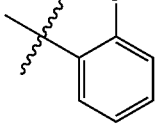 | 1-[[2-(3,4-Difluorophenyl)-4-quinolinyl]carbonyl]-pyrrolidine | 1.93 | 356.03 |
| 10 | H | 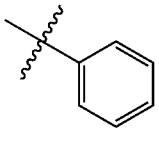 | 1-[[2-(2-Fluorophenyl)-4-quinolinyl]carbonyl]-pyrrolidine | 2.44 | 320.97 |
| 11 | F | 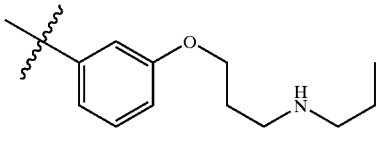 | 1-[[(6-Fluoro-2-phenyl)-4-quinolinyl]carbonyl]-pyrrolidine | 2.78 | 320.91 |
| 12 | H | 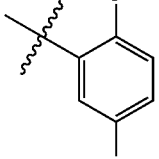 | 1-[[2-[3-(3-n-propylamino-1-propoxy)phenyl]-4-quinolinyl]carbonyl]-pyrrolidine | 2.59 | 338.99 |
| 13 | H | 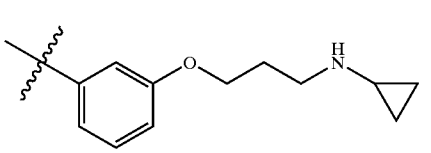 | 1-[[2-(2,5-Difluorophenyl)-4-quinolinyl]carbonyl]-pyrrolidine | | |
| 14 | H |  | 1-[[2-[3-(3-cyclopropylamino-1-propoxy)phenyl]-4-quinolinyl]carbonyl]-pyrrolidine | 2.15 | 430.05 |

TABLE 1-continued

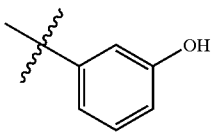

| Example Number | R1 | W | Compound Name | HPLC time (min) | [M + H]+ |
|---|---|---|---|---|---|
| 15 | H | 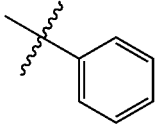 | 1-[[2-(3-Hydroxyphenyl)-4-quinolinyl]carbonyl]-pyrrolidine | | |
| 16 | Cl | 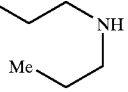 | 1-[[(6-Chloro-2-phenyl)-4-quinolinyl]carbonyl]-pyrrolidine | 2.42 | 317.03 |
| 17 | H | 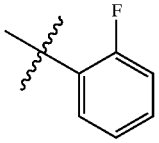 | 1-[[2-[4-(3-n-propylamino-1-propoxy)phenyl]-4-quinolinyl]carbonyl]-pyrrolidine | 2.18 | 436.14 |
| 18 | Cl | 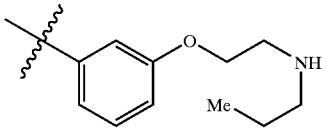 | 1-[[6-Chloro-2-(2-fluorophenyl)-4-quinolinyl]carbonyl]-pyrrolidine | 2.68 | 355.12 |
| 19 | H | 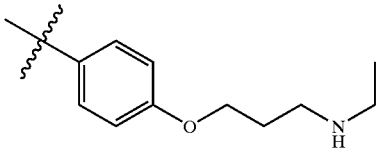 | 1-[[2-[3-(2-n-Propylamino-1-ethoxy)phenyl]-4-quinolinyl]carbonyl]-pyrrolidine | 2.07 | 404.17 |
| 20 | H | 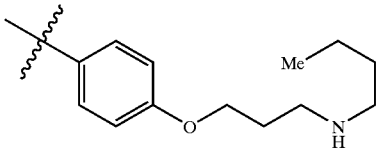 | 1-[[2-[4-(3-Ethylamino-1-propoxy)phenyl]-4-quinolinyl]carbonyl]-pyrrolidine | 2.12 | 422.13 |
| 21 | H | 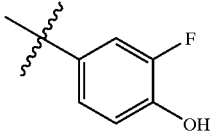 | 1-[[2-[4-(3-n-Butylamino-1-propoxy)phenyl]-4-quinolinyl]carbonyl]-pyrrolidine | 2.26 | 450.15 |
| 22 | H | | 1-[[2-(3-Fluoro-4-hydroxyphenyl)-4-quinolinyl]carbonyl]-pyrrolidine | | |

TABLE 1-continued

| Example Number | R1 | W | Compound Name | HPLC time (min) | [M + H]+ |
|---|---|---|---|---|---|
| 23 | H | (3-(2-methylaminoethoxy)phenyl) | 1-[[2-[3-(2-Methylamino-1-ethoxy)phenyl]-4-quinolinyl]carbonyl]-pyrrolidine | 1.97 | 376.15 |
| 24 | H | (2-fluoro-4-methoxyphenyl) | 1-[[2-(2-Fluoro-4-methoxyphenyl)-4-quinolinyl]carbonyl]-pyrrolidine | 2.45 | 351.08 |
| 25 | H | (3-(3-pyrrolidinylpropoxy)phenyl) | 1-[[2-[3-(3-N-Pyrrolidinyl-1-propoxy)phenyl]-4-quinolinyl]carbonyl]-pyrrolidine | 2.15 | 448.03 |
| 26 | H | (3-methoxyphenyl) | 1-[[2-(3-Methoxyphenyl)-4-quinolinyl]carbonyl]-pyrrolidine | | |
| 27 | H | (4-(3-i-propylaminopropoxy)phenyl) | 1-[[2-[4-(3-i-propylamino-1-propoxy)phenyl]-4-quinolinyl]carbonyl]-pyrrolidine | 2.26 | 450.05 |
| 28 | H | (3-(2-imidazolylethoxy)phenyl) | 1-[[2-[3-(2-Imidazolyl-1-ethoxy)phenyl]-4-quinolinyl]carbonyl]-pyrrolidine | 1.99 | 412.96 |

Examples 33–69

The following compounds were prepared by methods analogous to that of Example 1. These compounds have the structures shown below:

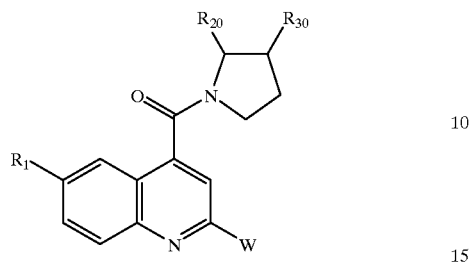

where $R_1$, $R_{20}$, $R_{30}$ and W are defined in the following Table 2. LC-MS data are given as HPLC retention times and $[M+H]^+$. The HPLC retention times shown in Table 1 were obtained by the method given in Example 1.

TABLE 2

| Example number | $R_1$ | $R_{20}$ | $R_{30}$ | W | Compound Name | HPLC time (min) | $[MH]^+$ |
|---|---|---|---|---|---|---|---|
| 33 | F | (±)-CH$_2$OH | H | 4-fluorophenyl | 1-[[6-Fluoro-2-(4-fluorophenyl)-4-quinolinyl]carbonyl]-2-hydroxymethyl-pyrrolidine | | |
| 34 | F | (R)-CH$_2$OH | H | 4-fluorophenyl | (R)-1-[[6-Fluoro-2-(4-fluorophenyl)-4-quinolinyl]carbonyl]-2-hydroxymethyl-pyrrolidine | | |
| 35 | F | (S)-CH$_2$OH | H | 4-fluorophenyl | (S)-1-[[6-Fluoro-2-(4-fluorophenyl)-4-quinolinyl]carbonyl]-2-hydroxymethyl-pyrrolidine | 2.56 | 369.05 |
| 36 | H | (±)-CH$_2$OH | H | 4-fluorophenyl | 1-[[2-(4-Fluorophenyl)-4-quinolinyl]carbonyl]-2-hydroxymethyl-pyrrolidine | | |

TABLE 2-continued

| Example number | R₁ | R₂₀ | R₃₀ | W | Compound Name | HPLC time (min) | [MH]⁺ |
|---|---|---|---|---|---|---|---|
| 37 | H | (R)-CH₂OH | H | 4-fluorophenyl | (R)-1-[[2-(4-Fluorophenyl)-4-quinolinyl]carbonyl]-2-hydroxymethyl-pyrrolidine | | |
| 38 | H | (S)-CH₂OH | H | 4-fluorophenyl | (S)-1-[[2-(4-Fluorophenyl)-4-quinolinyl]carbonyl]-2-hydroxymethyl-pyrrolidine | 2.42 | 350.99 |
| 39 | H | (±)-CH₂OH | H | 3,4-difluorophenyl | 1-[[2-(3,4-Difluorophenyl)-4-quinolinyl]carbonyl]-2-hydroxymethyl-pyrrolidine | | |
| 40 | H | (R)-CH₂OH | H | 3,4-difluorophenyl | (R)-1-[[2-(3,4-Difluorophenyl)-4-quinolinyl]carbonyl]-2-hydroxymethyl-pyrrolidine | | |
| 41 | H | (S)-CH₂OH | H | 3,4-difluorophenyl | (S)-1-[[2-(3,4-Difluorophenyl)-4-quinolinyl]carbonyl]-2-hydroxymethyl-pyrrolidine | 2.61 | 369.06 |
| 42 | Cl | (±)-CH₂OH | H | phenyl | 1-[(6-Chloro-2-phenyl-4-quinolinyl)carbonyl]-2-hydroxymethyl-pyrrolidine | | |
| 43 | Cl | (R)-CH₂OH | H | phenyl | (R)-1-[(6-Chloro-2-phenyl-4-quinolinyl)carbonyl]-2-hydroxymethyl-pyrrolidine | | |
| 44 | Cl | (S)-CH₂OH | H | phenyl | (S)-1-[(6-Chloro-2-phenyl-4-quinolinyl)carbonyl]-2-hydroxymethyl-pyrrolidine | 2.61 | 366.90 |

TABLE 2-continued

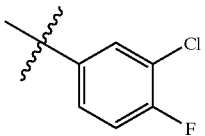

| Example number | R₁ | R₂₀ | R₃₀ | W | Compound Name | HPLC time (min) | [MH]⁺ |
|---|---|---|---|---|---|---|---|
| 45 | H | (±)-CH₂OH | H | 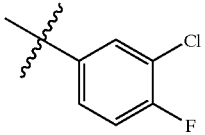 | 1-[[2-(3-Chloro-4-fluorophenyl)-4-quinolinyl]carbonyl]-2-hydroxymethyl-pyrrolidine | | |
| 46 | H | (R)-CH₂OH | H | 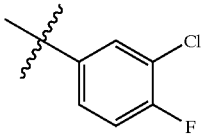 | (R)-1-[[2-(3-Chloro-4-fluorophenyl)-4-quinolinyl]carbonyl]-2-hydroxymethyl-pyrrolidine | | |
| 47 | H | (S)-CH₂OH | H | 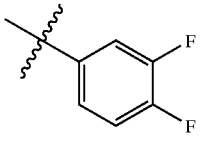 | (S)-1-[[2-(3-Chloro-4-fluorophenyl)-4-quinolinyl]carbonyl]-2-hydroxymethyl-pyrrolidine | 2.74 | 385.03 |
| 48 | F | (±)-CH₂OH | H | 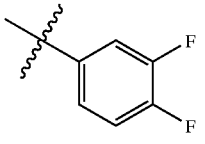 | 1-[[6-Fluoro-2-(3,4-difluorophenyl)-4-quinolinyl)carbonyl]-2-hydroxymethyl-pyrrolidine | | |
| 49 | F | (R)-CH₂OH | H | 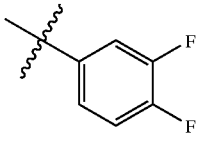 | (R)-1-[[6-Fluoro-2-(3,4-difluorophenyl)-4-quinolinyl)carbonyl]-2-hydroxymethyl-quinolinyl | | |
| 50 | F | (S)-CH₂OH | H | 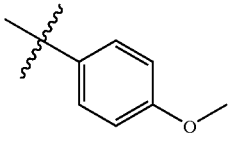 | (S)-1-[[6-Fluoro-2-(3,4-difluorophenyl)-4-quinolinyl)carbonyl]-2-hydroxymethyl-pyrrolidine | 2.69 | 387.06 |
| 51 | H | (±)-CH₂OH | H | 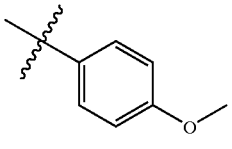 | 1-[[2-(4-Methoxyphenyl)-4-quinolinyl]carbonyl]-2-hydroxymethyl-pyrrolidine | | |
| 52 | H | (R)-CH₂OH | H | 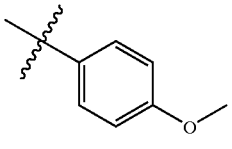 | (R)-1-[[2-(4-Methoxyphenyl)-4-quinolinyl]carbonyl]-2-hydroxymethyl-pyrrolidine | | |

TABLE 2-continued

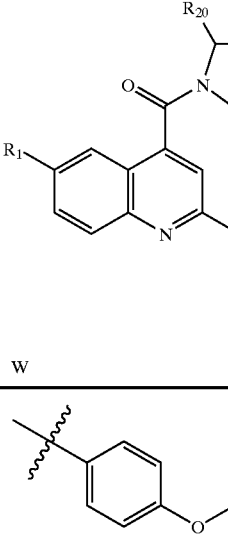

| Example number | R₁ | R₂₀ | R₃₀ | W | Compound Name | HPLC time (min) | [MH]⁺ |
|---|---|---|---|---|---|---|---|
| 53 | H | (S)-CH₂OH | H | 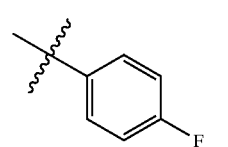 | (S)-1-[[2-(4-Methoxyphenyl)-4-quinolinyl]carbonyl]-2-hydroxymethyl-pyrrolidine | 2.14 | 362.97 |
| 54 | Cl | (±)-CH₂OH | H | 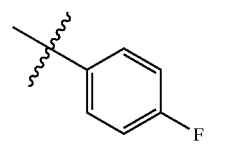 | 1-[[6-Fluoro-2-(4-fluorophenyl)-4-quinolinyl)carbonyl]-2-hydroxymethyl-pyrrolidine | | |
| 55 | Cl | (R)-CH₂OH | H | 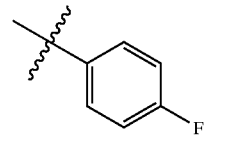 | (R)-1-[[6-Fluoro-2-(4-fluorophenyl)-4-quinolinyl)carbonyl]-2-hydroxymethyl-pyrrolidine | | |
| 56 | Cl | (S)-CH₂OH | H | 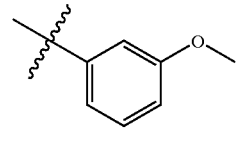 | (S)-1-[[6-Fluoro-2-(4-fluorophenyl)-4-quinolinyl)carbonyl]-2-hydroxymethyl-pyrrolidine | 2.59 | 384.96 |
| 57 | H | (±)-CH₂OH | H | 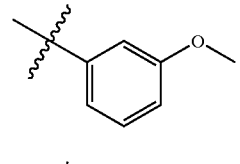 | 1-[[2-(3-Methoxyphenyl)-4-quinolinyl]carbonyl]-2-hydroxymethyl-pyrrolidine | | |
| 58 | H | (R)-CH₂OH | H | 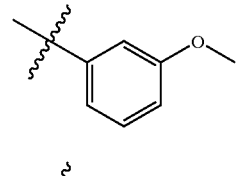 | (R)-1-[[2-(3-Methoxyphenyl)-4-quinolinyl]carbonyl]-2-hydroxymethyl-pyrrolidine | | |
| 59 | H | (S)-CH₂OH | H | 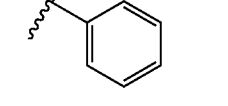 | (S)-1-[[2-(3-Methoxyphenyl)-4-quinolinyl]carbonyl]-2-hydroxymethyl-pyrrolidine | 2.36 | 362.98 |
| 60 | F | (±)-CH₂OH | H |  | 1-[(6-Fluoro-2-phenyl-4-quinolinyl)carbonyl]-2-hydroxymethyl-pyrrolidine | | |

TABLE 2-continued

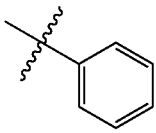

| Example number | R₁ | R₂₀ | R₃₀ | W | Compound Name | HPLC time (min) | [MH]⁺ |
|---|---|---|---|---|---|---|---|
| 61 | F | (R)-CH₂OH | H | 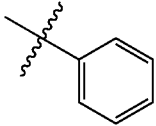 | (R)-1-[(6-Fluoro-2-phenyl-4-quinolinyl)carbonyl]-2-hydroxymethyl-pyrrolidine | | |
| 62 | F | (S)-CH₂OH | H | 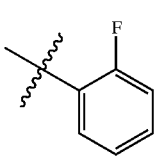 | (S)-1-[(6-Fluoro-2-phenyl-4-quinolinyl)carbonyl]-2-hydroxymethyl-pyrrolidine | 2.47 | 351.07 |
| 63 | H | (±)-CH₂OH | H | 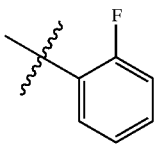 | 1-[[2-(2-Fluorophenyl)-4-quinolinyl]carbonyl]-2-hydroxymethyl-pyrrolidine | | |
| 64 | H | (R)-CH₂OH | H | 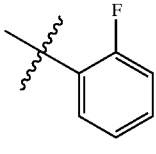 | (R)-1-[[2-(2-Fluorophenyl)-4-quinolinyl]carbonyl]-2-hydroxymethyl-pyrrolidine | | |
| 65 | H | (S)-CH₂OH | H | 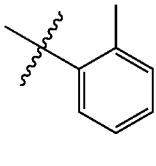 | (S)-1-[[2-(2-Fluorophenyl)-4-quinolinyl]carbonyl]-2-hydroxymethyl-pyrrolidine | 2.31 | 351.06 |
| 66 | H | (±)-CH₂OH | H | 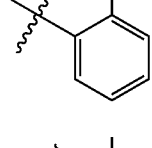 | 1-[[2-(2-Methylphenyl)-4-quinolinyl]carbonyl]-2-hydroxymethyl-pyrrolidine | | |
| 67 | H | (R)-CH₂OH | H | 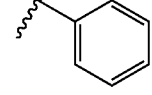 | (R)-1-[[2-(2-Methylphenyl)-4-quinolinyl]carbonyl]-2-hydroxymethyl-pyrrolidine | | |
| 68 | H | (S)-CH₂OH | H | | (S)-1-[[2-(2-Methylphenyl)-4-quinolinyl]carbonyl]-2-hydroxymethyl-pyrrolidine | 2.38 | 347.04 |

TABLE 2-continued

| Example number | R₁ | R₂₀ | R₃₀ | W | Compound Name | HPLC time (min) | [MH]⁺ |
|---|---|---|---|---|---|---|---|
| 69 | Cl | (±)-CH₂OH | H | 2-fluorophenyl | 1-[[6-Fluoro-2-(2-fluorophenyl)-4-quinolinyl)carbonyl]-2-hydroxymethyl-pyrrolidine | | |
| 70 | Cl | (R)-CH₂OH | H | 2-fluorophenyl | (R)-1-[[6-Fluoro-2-(2-fluorophenyl)-4-quinolinyl)carbonyl]-2-hydroxymethyl-pyrrolidine | | |
| 71 | Cl | (S)-CH₂OH | H | 2-fluorophenyl | (S)-1-[[6-Fluoro-2-(2-fluorophenyl)-4-quinolinyl)carbonyl]-2-hydroxymethyl-pyrrolidine | 2.72 | 385.04 |
| 72 | F | (±)-CH₂OH | H | 3-thienyl | 1-[[6-Fluoro-2-(3-thienyl)-4-quinolinyl)carbonyl]-2-hydroxymethyl-pyrrolidine | | |
| 73 | F | (R)-CH₂OH | H | 3-thienyl | (R)-1-[[6-Fluoro-2-(3-thienyl)-4-quinolinyl)carbonyl]-2-hydroxymethyl-pyrrolidine | | |
| 74 | F | (S)-CH₂OH | H | 3-thienyl | (S)-1-[[6-Fluoro-2-(3-thienyl)-4-quinolinyl)carbonyl]-2-hydroxymethyl-pyrrolidine | 2.41 | 357.06 |
| 75 | H | (±)-CH₂OH | H | phenyl | 1-[[2-Phenyl-4-quinolinyl]carbonyl]-2-hydroxymethyl-pyrrolidine | | |
| 76 | H | (R)-CH₂OH | H | phenyl | (R)-1-[[2-Phenyl-4-quinolinyl]carbonyl]-2-hydroxymethyl-pyrrolidine | | |

TABLE 2-continued

| Example number | R₁ | R₂₀ | R₃₀ | W | Compound Name | HPLC time (min) | [MH]⁺ |
|---|---|---|---|---|---|---|---|
| 77 | H | (S)-CH₂OH | H | phenyl | (S)-1-[[2-Phenyl-4-quinolinyl]carbonyl]-2-hydroxymethyl-pyrrolidine | 2.27 | 333.04 |
| 78 | H | (±)-CH₂OH | H | 2-fluoro-4-hydroxyphenyl | 1-[[2-(2-Fluoro-4-hydroxyphenyl)-4-quinolinyl]carbonyl]-2-hydroxymethyl-pyrrolidine | | |
| 79 | H | (R)-CH₂OH | H | 2-fluoro-4-hydroxyphenyl | (R)-1-[[2-(2-Fluoro-4-hydroxyphenyl)-4-quinolinyl]carbonyl]-2-hydroxymethyl-pyrrolidine | | |
| 80 | H | (S)-CH₂OH | H | 2-fluoro-4-hydroxyphenyl | (S)-1-[[2-(2-Fluoro-4-hydroxyphenyl)-4-quinolinyl]carbonyl]-2-hydroxymethyl-pyrrolidine | 2.04 | 367.09 |
| 81 | H | (±)-CH₂OH | H | 2,4-difluorophenyl | 1-[[2-(2,4-Difluorophenyl)-4-quinolinyl]carbonyl]-2-hydroxymethyl-pyrrolidine | | |
| 82 | H | (R)-CH₂OH | H | 2,4-difluorophenyl | (R)-1-[[2-(2,4-Difluorophenyl)-4-quinolinyl]carbonyl]-2-hydroxymethyl-pyrrolidine | | |
| 83 | H | (S)-CH₂OH | H | 2,4-difluorophenyl | (S)-1-[[2-(2,4-Difluorophenyl)-4-quinolinyl]carbonyl]-2-hydroxymethyl-pyrrolidine | 2.40 | 368.89 |

TABLE 2-continued

| Example number | R$_1$ | R$_{20}$ | R$_{30}$ | W | Compound Name | HPLC time (min) | [MH]$^+$ |
|---|---|---|---|---|---|---|---|
| 84 | H | (±)-CH$_2$OH | H | 2-Fluoro-4-ethoxyphenyl | 1-[[2-(2-Fluoro-4-ethoxyphenyl)-4-quinolinyl]carbonyl]-2-hydroxymethyl-pyrrolidine | | |
| 85 | H | (R)-CH$_2$OH | H | 2-Fluoro-4-ethoxyphenyl | (R)-1-[[2-(2-Fluoro-4-ethoxyphenyl)-4-quinolinyl]carbonyl]-2-hydroxymethyl-pyrrolidine | | |
| 86 | H | (S)-CH$_2$OH | H | 2-Fluoro-4-ethoxyphenyl | (S)-1-[[2-(2-Fluoro-4-ethoxyphenyl)-4-quinolinyl]carbonyl]-2-hydroxymethyl-pyrrolidine | 2.54 | 395.00 |
| 87 | H | (±)-CH$_2$OH | H | 2,6-Difluorophenyl | 1-[[2-(2,6-Difluorophenyl)-4-quinolinyl]carbonyl]-2-hydroxymethyl-pyrrolidine | | |
| 88 | H | (R)-CH$_2$OH | H | 2,6-Difluorophenyl | (R)-1-[[2-(2,6-Doifluorophenyl)-4-quinolinyl]carbonyl]-2-hydroxymethyl-pyrrolidine | | |
| 89 | H | (S)-CH$_2$OH | H | 2,6-Difluorophenyl | (S)-1-[[2-(2,6-Difluorophenyl)-4-quinolinyl]carbonyl]-2-hydroxymethyl-pyrrolidine | 2.21 | 368.94 |
| 90 | Br | (±)-CH$_2$OH | H | phenyl | 1-[[6-Bromo-2-phenyl-4-quinolinyl)carbonyl]-2-hydroxymethyl-pyrrolidine | | |

TABLE 2-continued

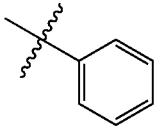

| Example number | R₁ | R₂₀ | R₃₀ | W | Compound Name | HPLC time (min) | [MH]⁺ |
|---|---|---|---|---|---|---|---|
| 91 | Br | (R)-CH₂OH | H | 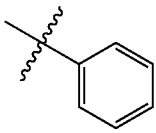 | (R)-1-[[6-Bromo-2-phenyl-4-quinolinyl)carbonyl]-2-hydroxymethyl-pyrrolidine | | |
| 92 | Br | (S)-CH₂OH | H | 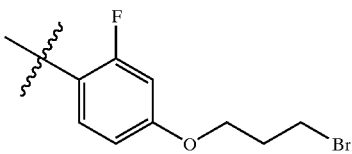 | (S)-1-[[6-Bromo-2-phenyl-4-quinolinyl)carbonyl]-2-hydroxymethyl-pyrrolidine | 2.68 | 410.82 |
| 93 | H | (±)-CH₂OH | H | 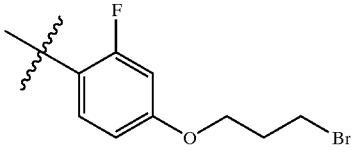 | 1-[[2-[2-Fluoro-4-(3-bromo-1-propoxy)phenyl)-4-quinolinyl]carbonyl]-2-hydroxymethyl-pyrrolidine | | |
| 94 | H | (R)-CH₂OH | H | 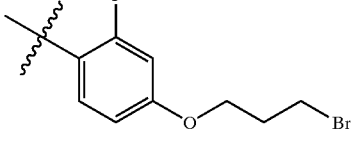 | (R)-1-[[2-[2-Fluoro-4-(3-bromo-1-propoxy)phenyl)-4-quinolinyl]carbonyl]-2-hydroxymethyl-pyrrolidine | | |
| 95 | H | (S)-CH₂OH | H | 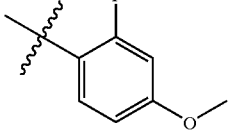 | (S)-1-[[2-[2-Fluoro-4-(3-bromo-1-propoxy)phenyl)-4-quinolinyl]carbonyl]-2-hydroxymethyl-pyrrolidine | 2.75 | 458.92 |
| 96 | H | (±)-CH₂OH | H | 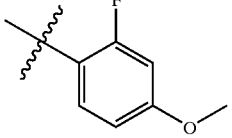 | 1-[[2-(2-Fluoro-4-methoxyphenyl)-4-quinolinyl]carbonyl]-2-hydroxymethyl-pyrrolidine | | |
| 97 | H | (R)-CH₂OH | H | 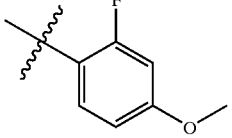 | (R)-1-[[2-(2-Fluoro-4-methoxyphenyl)-4-quinolinyl]carbonyl]-2-hydroxymethyl-pyrrolidine | | |

TABLE 2-continued

| Example number | R₁ | R₂₀ | R₃₀ | W | Compound Name | HPLC time (min) | [MH]⁺ |
|---|---|---|---|---|---|---|---|
| 98 | H | (S)-CH₂OH | H | 2-F, 4-OMe phenyl | (S)-1-[[2-(2-Fluoro-4-methylphenyl)-4-quinolinyl]carboinyl]-2-hydroxymethyl-pyrrolidine | 2.31 | 380.97 |
| 99 | H | (±)-CH₂OH | H | 2,5-difluorophenyl | 1-[[2-(2,5-Difluorophenyl)-4-quinolinyl]carbonyl]-2-hydroxymethylpyrrolidine | | |
| 100 | H | (R)-CH₂OH | H | 2,5-difluorophenyl | (R)-1-[[2-(2,5-Difluorophenyl)-4-quinolinyl]carbonyl]-2-hydroxymethylpyrrolidine | | |
| 101 | H | (S)-CH₂OH | H | 2,5-difluorophenyl | (S)-1-[[2-(2,5-Difluorophenyl)-4-quinolinyl]carbonyl]-2-hydroxymethylpyrrolidine | | |
| 102 | OMe | (±)-CH₂OH | H | phenyl | 1-[[6-Methoxy-2-phenyl-4-quinolinyl)carbonyl]-2-hydroxymethylpyrrolidine | | |
| 103 | OMe | (R)-CH₂OH | H | phenyl | (R)-1-[[6-Methoxy-2-phenyl-4-quinolinyl)carbonyl]-2-hydroxymethylpyrrolidine | | |
| 104 | OMe | (S)-CH₂OH | H | phenyl | (S)-1-[[6-Methoxy-2-phenyl-4-quinolinyl)carbonyl]-2-hydroxymethylpyrrolidine | | |

TABLE 2-continued

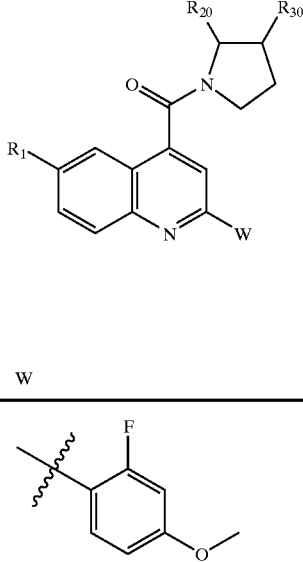

| Example number | R₁ | R₂₀ | R₃₀ | W | Compound Name | HPLC time (min) | [MH]⁺ |
|---|---|---|---|---|---|---|---|
| 105 | Cl | (±)-CH₂OH | H | 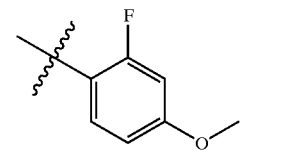 | 1-[[6-Chloro-2-(2-fluoro-4-methoxyphenyl)-4-quinolinyl]carbonyl]-2-hydroxymethyl pyrrolidine | | |
| 106 | Cl | (R)-CH₂OH | H | 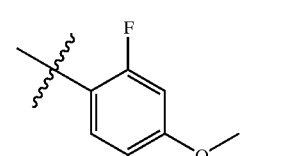 | (R)-1-[[6-Chloro-2-(2-fluoro-4-methoxyphenyl) 4-quinolinyl]carbonyl]-2-hydroxymethyl-pyrrolidine | | |
| 107 | Cl | (S)-CH₂OH | H | 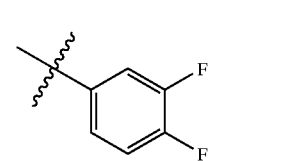 | (S)-1-[[6-Chloro-2-(2-fluoro-4-methoxyphenyl)-4-quinolinyl]carbonyl]-2-hydroxymethyl pyrrolidine | | |
| 108 | H | (±)-CH₂N(CH₃)CH₂CH₂N(C₂H₅)₂ | H | 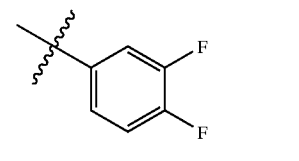 | 1-[[2-(3,4-Difluorophenyl)-4-quinolinyl]carbonyl]-{[(2-Diethylamino-ethyl)-methyl-amino]-methyl}-pyrrolidine | | |
| 109 | H | (R)-CH₂N(CH₃)CH₂CH₂N(C₂H₅)₂ | H | 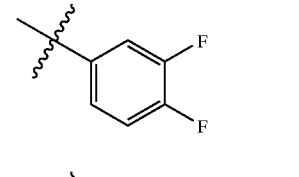 | (R)-1-[[2-(3,4-Difluorophenyl)-4-quinolinyl]carbonyl]-2-{[(2-Diethylamino-ethyl)-methyl-amino]-methyl}-pyrrolidine | | |
| 110 | H | (S)-CH₂N(CH₃)CH₂CH₂N(C₂H₅)₂ | H | 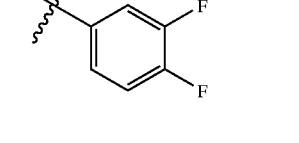 | (S)-1-[[2-(3,4-Difluorophenyl)-4-quinolinyl]carbonyl]-2-{[(2-Diethylamino-ethyl)-methyl-amino]-methyl}-pyrrolidine | 2.34 | 481.09 |
| 111 | H | Et-N(piperazine)- | H | 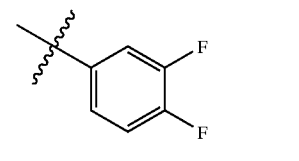 | 1-[[2-(3,4-Difluorophebnyl)-4-quinolinyl]carbonyl]-2-(N-ethylpiperazinyl)methyl)-pyrrolidine | | |

TABLE 2-continued

| Example number | R$_1$ | R$_{20}$ | R$_{30}$ | W | Compound Name | HPLC time (min) | [MH]$^+$ |
|---|---|---|---|---|---|---|---|
| 112 | H | (R)-Et-N-piperazinyl-CH$_2$- | H | 3,4-difluorophenyl | (R)-1-[[2-(3,4-Difluorophenyl)-4-quinolinyl]carbonyl]-2-(N-ethylpiperazinyl)methyl)-pyrrolidine | | |
| 113 | H | (S)-Et-N-piperazinyl-CH$_2$- | H | 3,4-difluorophenyl | (S)-1-[[2-(3,4-Difluorophenyl)-4-quinolinyl]carbonyl]-2-(N-ethylpiperazinyl)methyl)-pyrrolidine | 2.35 | 465.06 |
| 114 | H | (±)-CH$_2$N(C$_2$H$_5$)CH$_2$CH$_2$N(C$_2$H$_5$)$_2$ | H | 3,4-difluorophenyl | 1-[[2-(3,4-Difluorophenyl)-4-quinolinyl]carbonyl]-2-{[(2-Diethylamino-ethyl)-ethyl-amino]-methyl}-pyrrolidine | | |
| 115 | H | (R)-CH$_2$N(C$_2$H$_5$)CH$_2$CH$_2$N(C$_2$H$_5$)$_2$ | H | 3,4-difluorophenyl | (R)-1-[[2-(3,4-Difluorophenyl)-4-quinolinyl]carbonyl]-2-{[(2-Diethylamino-ethyl)-ethyl-amino]-methyl}-pyrrolidine | | |
| 116 | H | (S)-CH$_2$N(C$_2$H$_5$)CH$_2$CH$_2$N(C$_2$H$_5$)$_2$ | H | 3,4-difluorophenyl | (S)-1-[[2-(3,4-Difluorophenyl)-4-quinolinyl]carbonyl]-2-{[(2-Diethylamino-ethyl)-ethyl-amino]-methyl}-pyrrolidine | 2.37 | 467.06 |
| 117 | H | (±)-CH$_2$N(CH$_2$)$_2$N(C$_2$H$_5$)$_2$ | H | 3,4-difluorophenyl | 1-[[2-(3,4-Difluorophenyl)-4-quinolinyl]carbonyl]-2-[(2-Diethylamino-ethylamino)-methyl]-pyrrolidine | | |
| 118 | H | (R)-CH$_2$NH(CH$_2$)$_2$N(C$_2$H$_5$)$_2$ | H | 3,4-difluorophenyl | (R)-1-[[2-(3,4-Difluorophenyl)-4-quinolinyl]carbonyl]-2-[(2-Diethylamino-ethylamino)-methyl]-pyrrolidine | | |

TABLE 2-continued

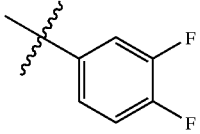

| Example number | $R_1$ | $R_{20}$ | $R_{30}$ | W | Compound Name | HPLC time (min) | [MH]+ |
|---|---|---|---|---|---|---|---|
| 119 | H | (S)-CH$_2$NH(CH$_2$)$_2$N(C$_2$H$_5$)$_2$ | H | 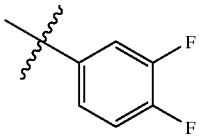 | (S)-1-[[2-(3,4-Difluorophenyl)-4-quinolinyl]carbonyl]-2-[(2-Diethylamino-ethylamino)-methyl]-pyrrolidine | 2.30 | 439.06 |
| 120 | H | (±)-CH$_2$NH(CH$_2$)$_2$N(CH$_3$)$_2$ | H | 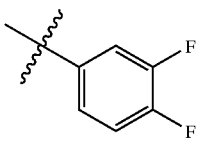 | 1-[[2-(3,4-Difluorophenyl)-4-quinolinyl]carbonyl]-2-[(2-Diethylamino-ethylamino)-methyl]-pyrrolidine | | |
| 121 | H | (R)-CH$_2$NH(CH$_2$)$_2$N(CH$_3$)$_2$ | H | 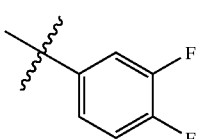 | (R)-1-[[2-(3,4-Difluorophenyl)-4-quinolinyl]carbonyl]-2-[(2-Diethylamino-ethylamino)-methyl]-pyrrolidine | | |
| 122 | H | (S)-CH$_2$NH(CH$_2$)$_2$N(CH$_3$)$_2$ | H | 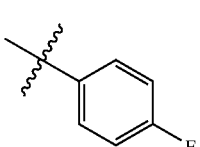 | (S)-1-[[2-(3,4-Difluorophenyl)-4-quinolinyl]carbonyl]-2-[(2-Diethylamino-ethylamino)-methyl]-pyrrolidine | 2.31 | 453.11 |
| 123 | H | (±)-CH$_2$NH(CH$_2$)$_2$N(CH$_3$)$_2$ | H | 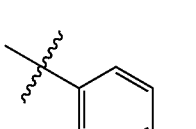 | 1-[[2-(4-Fluorophenyl)-4-quinolinyl]carbonyl]-2-[(2-Dimethylamino-ethylamino)-methyl]-pyrrolidine | | |
| 124 | H | (R)-CH$_2$NH(CH$_2$)$_2$N(CH$_3$)$_2$ | H | 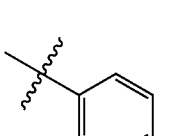 | (R)-1-[[2-(4-Fluorophenyl)-4-quinolinyl]carbonyl]-2-[(2-Diethylamino-ethylamino)-methyl]-pyrrolidine | | |
| 125 | H | (S)-CH$_2$NH(CH$_2$)$_2$N(CH$_3$)$_2$ | H | | (S)-1-[[2-(4-Fluorophenyl)-4-quinolinyl]carbonyl]-2-[(2-Dimethylamino-ethylamino)-methyl]-pyrrolidine | 2.19 | 421.18 |

TABLE 2-continued

| Example number | R₁ | R₂₀ | R₃₀ | W | Compound Name | HPLC time (min) | [MH]⁺ |
|---|---|---|---|---|---|---|---|
| 126 | H | 4-methyl-[1,4]diazepan-1-ylmethyl | H | 3,4-difluorophenyl | 1-[[2-(3,4-Difluorophenyl)-4-quinolinyl]carbonyl]-2-(4-methyl-[1,4]diazepan-1-ylmethyl)-pyrrolidine | | |
| 127 | H | 4-methyl-[1,4]diazepan-1-ylmethyl | H | 3,4-difluorophenyl | (R)-1-[[2-(3,4-Difluorophenyl)-4-quinolinyl]carbonyl]-2-(4-methyl-[1,4]diazepan-1-ylmethyl)-pyrrolidine | | |
| 128 | H | 4-methyl-[1,4]diazepan-1-ylmethyl | H | 3,4-difluorophenyl | (S)-1-[[2-(3,4-Difluorophenyl)-4-quinolinyl]carbonyl]-2-(4-methyl-[1,4]diazepan-1-ylmethyl)-pyrrolidine | 2.30 | 465.13 |
| 129 | H | 4-methyl-piperazin-1-ylmethyl | H | 3,4-difluorophenyl | 1-[[2-(3,4-Difluorophenyl)-4-quinolinyl]carbonyl]-2-(4-methyl-pipoerazin-1-ylmethyl)-pyrrolidine | | |
| 130 | H | 4-methyl-piperazin-1-ylmethyl | H | 3,4-difluorophenyl | (R)-1-[[2-(3,4-Difluorophenyl)-4-quinolinyl]carbonyl]-2-(4-methyl-piperazin-1-ylmethyl)-pyrroldine | | |
| 131 | H | 4-methyl-piperazin-1-ylmethyl | H | 3,4-difluorophenyl | (S)-1-[[2-(3,4-Difluorophenyl)-4-quinolinyl]carbinyl]-2-(4-methyl-piperazin-1-ylmethyl)-methyl)-pyrrolidine | | |

TABLE 2-continued

| Example number | R$_1$ | R$_{20}$ | R$_{30}$ | W | Compound Name | HPLC time (min) | [MH]$^+$ |
|---|---|---|---|---|---|---|---|
| 132 | H | piperidin-1-yl-ethyl-HN-CH$_2$- | H | 3,4-difluorophenyl | 1-[[2-(3,4-Difluorophenyl)-4-quinolinyl]carbonyl]-2-[(2-piperidin-1-yl-ethylamino)-methyl]-pyrrolidine | | |
| 133 | H | piperidin-1-yl-ethyl-HN-CH$_2$- | H | 3,4-difluorophenyl | (R)-1-[[2-(3,4-Difluorophenyl)-4-quinolinyl]carbonyl]-2-[(2-piperidin-1-yl ethylamino)-methyl]-pyrrolidine | | |
| 134 | H | piperidin-1-yl-ethyl-HN-CH$_2$- | H | 3,4-difluorophenyl | (S)-1-[[2-(3,4-Difluorophenyl)-4-quinolinyl]carbonyl]-2-[(2-piperidin-1-yl-ethylamino)-methyl-pyrrolidine | 2.43 | 465.04 |
| 135 | H | pyrrolidin-1-yl-ethyl-HN-CH$_2$- | H | 3,4-difluorophenyl | 1-[[2-(3,4-Difluorophenyl)-4-quinolinyl]carbonyl]-2-[(2-pyrrolidin-1-yl-ethylamino)-methyl]-pyrrolidine | | |

TABLE 2-continued

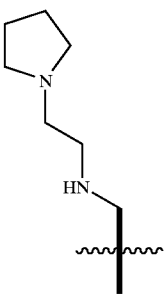

| Example number | R₁ | R₂₀ | R₃₀ | W | Compound Name | HPLC time (min) | [MH]⁺ |
|---|---|---|---|---|---|---|---|
| 136 | H | 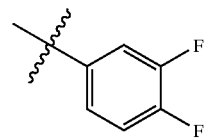 | H | 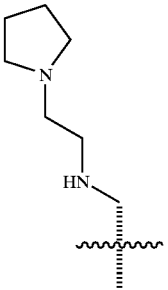 | (R)-1-[[2-(3,4-Difluorophenyl)-4-quinolinyl]carbonyl]-2-[(2-pyrrolidin-1-yl-ethylamino)-methyl]-pyrrolidine | | |
| 137 | H | 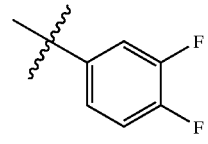 | H | 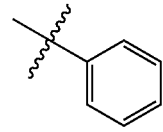 | (S)-1-[[2-(3,4-Difluorophenyl)-4-quinolinyl]carbonyl]-2-[(2-pyrrolidin-1-yl-ethylamino)-methyl]-pyrrolidine | | |
| 138 | H | (±)-CH₂OH | H | 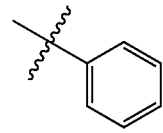 | 1-[(2-phenyl-4-quinolinyl)carbonyl]-2-hydroxymethyl-pyrrolidine | | |
| 139 | H | (R)-CH₂OH | H | 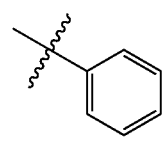 | (R)-1-[(2-phenyl-4-quinolinyl)carbonyl]-2-hydroxymethyl-pyrrolidine | | |
| 140 | H | (S)-CH₂OH | H | 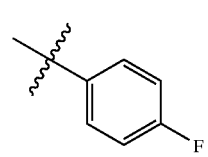 | (S)-1-[(2-phenyl-4-quinolinyl)carbonyl]-2-hydroxymethyl-pyrrolidine | | |
| 141 | H | H | (±) —OH |  | 1-[[2-(4-Fluorophenyl)-4-quinolinyl]carbonyl]-3-hydroxy-pyrrolidine | | |

TABLE 2-continued

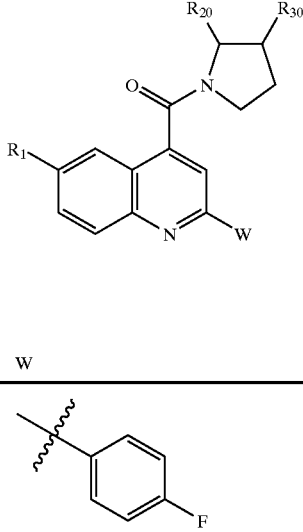

| Example number | R₁ | R₂₀ | R₃₀ | W | Compound Name | HPLC time (min) | [MH]⁺ |
|---|---|---|---|---|---|---|---|
| 142 | H | H | (R)<br>—OH | 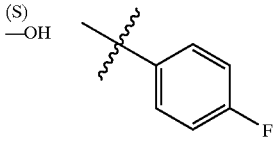 | (R)-1-[[2-(4-Fluorophenyl)-4-quinolinyl]carbonyl]-3-hydroxy-pyrrolidine | | |
| 143 | H | H | (S)<br>—OH | | (S)-1-[[2-(4-Fluorophenyl)-4-quinolinyl]carbonyl]-3-hydroxy-pyrrolidine | 2.32 | 336.93 |

Example 144

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

Example 145

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 146

Binding Assay

This assay is a standard assay for $GABA_A$ binding affinity. The high affinity and high selectivity of compounds of this invention for the benzodiazepine site of the $GABA_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000× g for 20 minutes. The supernatant is decanted, the pellet rehomogenized in the same volume of buffer, and centrifuged again at 20,000× g. The supernatant of this centrifugation step is decanted and the pellet is stored at –20° C. overnight. The pellet is then thawed and resuspended in 25 volumes of Buffer A (original wt/vol), centrifuged at 20,000× g and the supernatant decanted. This wash step is repeated once. The pellet is finally resuspended in 50 volumes of Buffer A.

Incubations containing 100 μl of tissue homogenate, 100 μl of radioligand, (0.5 nM $^{3}H$-Ro15-1788 [$^{3}H$-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 μM Diazepam (Research Biochemicals International, Natick, Mass.). Data were collected in triplicate, averaged, and percent inhibition of total specific binding (Total Specific Binding=Total–Nonspecific) was calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. When tested using this assay, preferred compounds of Formula I exhibit $K_i$ values of less than 1 uM, more preferred compounds of the invention have $K_i$ values of less than 500 nM, and particularly preferred compounds have $K_i$ values of less than 100 nM.

Example 147

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of –70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM–9 μM). Each oocyte is exposed to increasing concentrations of compound in order to evaluate a concentration/effect relationship. Compound efficacy is calculated as a percent-change in current amplitude: 100*((Ic/I)–1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

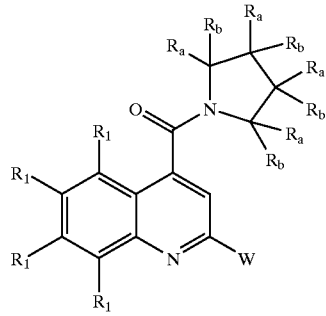

or a pharmaceutically acceptable salt thereof wherein:

$R_1$ at each occurrence is independently selected from the group consisting of hydrogen, halogen, cyano, haloalkyl, haloalkoxy, hydroxy, amino, —NH($R_2$), —N($R_2$)$_2$, nitro, $C_1$–$C_8$ alkoxy and $R_2$;

$R_2$ at each occurrence is independently selected from the group consisting of $C_1$–$C_8$ alkyl, $C_2$–$C_8$ alkenyl, $C_2$–$C_8$ alkynyl, $C_3$–$C_8$ cycloalkyl, $C_3$–$C_8$ cycloalkenyl, and $C_5$–$C_{10}$ cycloalkynyl;

at least one of $R_a$ or $R_b$ is selected from halogen, cyano, nitro, haloalkyl, haloalkoxy, hydroxy, amino, phenyl substituted with 0–3 $R_6$, —$XR_7$, Y, $R_2$, —$OR_2$ —NH ($R_2$) and —N($R_2$)$_2$, wherein each $R_2$ group is independently substituted with from 0 to 2 $R_6$;

the remaining $R_a$ and $R_b$ at each occurrence are independently selected from the group consisting of hydrogen, halogen, cyano, nitro, haloalkyl, haloalkoxy, hydroxy, amino, —$OR_2$ wherein $R_2$ is substituted with 0–2 $R_6$, —NH($R_2$) wherein $R_2$ is substituted with 0–2 $R_6$, —N($R_2$)$_2$ wherein the $R_2$ groups are independently substituted with 0–2 $R_6$, $R_2$ wherein the $R_2$ group is substituted with 0–2 $R_6$, phenyl substituted with 0–3 $R_6$, —$XR_7$, and Y;

W represents phenyl, thienyl, or pyridyl, wherein each is substituted with $R_{d}$, $R_{d'}$, and $R_{d''}$ which are independently selected from the group consisting of hydrogen, halogen, cyano, nitro, haloalkyl, haloalkoxy, hydroxy, amino, $R_2$ substituted with 0–2 $R_6$, —$OR_2$ substituted with 0–2 $R_6$, —NH($R_2$) wherein $R_2$ is substituted with 0–2 $R_6$, phenyl substituted with 0–3 $R_6$, —$XR_7$, Y, and —N($C_1$–$C_6$ alkyl$_1$) ($C_1$–$C_6$ alkyl$_2$) where each alkyl is independently substituted with 0–2 $R_6$, or alkyl$_1$, alkyl$_2$ and the nitrogen to which they are attached form a heterocycloalkyl ring substituted with 0–2 $R_6$;

X at each occurrence is independently selected from the group consisting of —$CH_2$—, —$CHR_8$—, —O—, —S(O)$_m$—, —NH—, —$NR_8$—, —C(O)—, —C(O) O—, —C(O)NH—, —C(O)$NR_8$—, —S(O)$_m$NH—, —S(O)$_m$NR$_8$—, —NHC(O)—, —NR$_8$C(O)—, —NHS(O)$_m$—, and —NR$_8$S(O)$_m$—; wherein m is 0, 1, or 2;

R$_6$ at each occurrence is independently selected from the group consisting of halogen, hydroxy, R$_2$, —OR$_2$, —NH(R$_2$), —N(R$_2$)$_2$, —NH—(R$_2$—Y), —N(R$_2$)—(R$_2$—Y), —NH—(R$_2$—N(R$_2$) (R$_2$)), —N(R$_2$)—(R$_2$—N(R$_2$) (R$_2$)), morpholinyl, pyrrolidinyl, piperidinyl, thiomorpholinyl, piperazinyl, homopiperazinyl, —S(O)$_m$(R$_2$), haloalkyl, haloalkoxy, —CO(R$_2$), —CONH(R$_2$), CON(R$_2$)$_2$, —XR$_7$, and Y;
wherein m is 0, 1, or 2;

R$_7$ and R$_8$ at each occurrence independently carry the same definition as R$_2$, wherein R$_7$ and R$_8$ are substituted with 0, 1, 2, 3, or 4 substituents selected from the group consisting of oxo, hydroxy, halogen, amino, cyano, nitro, haloalkyl, haloalkoxy, —O(R$_2$), —NH(R$_2$), —N(R$_2$)$_2$, —NHC(O) (R$_2$), —N (R$_2$)C(O)(R$_2$), —NHS(O)$_m$(R$_2$), —S(O)$_m$(R$_2$), —S(O)$_m$NH(R$_2$), and —S(O)$_m$N(R$_2$)$_2$, and Y';
wherein m is 0, 1, or 2; and Y and Y' at each occurrence are independently selected from 5- to 8-membered carbocycles and heterocycles, which are saturated, partially unsaturated, or aromatic, and contain zero, one or two heteroatoms selected from N, O, and S, and which carbocycles and heterocycles may be further substituted with 1, 2, 3, or 4 substituents selected from the group consisting of halogen, oxo, hydroxy, amino, nitro, cyano, R$_2$, —OR$_2$, —NH(R$_2$), —N(R$_2$)$_2$, and —S(O)$_a$(R$_2$);
wherein
a is 0, 1, or 2.

2. A compound of the formula

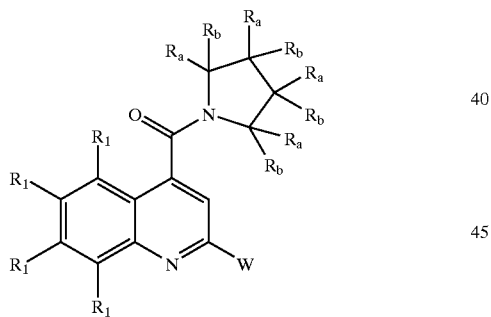

or a pharmaceutically acceptable salt thereof wherein:
R$_1$ at each occurrence is independently selected from the group consisting of hydrogen, C$_1$–C$_6$ alkyl, halogen, cyano, haloalkyl, haloalkoxy, hydroxy, amino, —NH(C$_1$–C$_6$ alkyl), and —N(C$_1$–C$_6$ alkyl) (C$_1$–C$_6$ alkyl);

at least one of R$_a$ or R$_b$ is selected from halogen, cyano, nitro, haloalkyl, haloalkoxy, hydroxy, amino, phenyl substituted with from 0 to 3 R$_6$, —XR$_7$, Y, C$_1$–C$_6$ alkyl, —O(C$_1$–C$_6$ alkyl), —NH(C$_1$–C$_6$ alkyl) and —N(C$_1$–C$_6$ alkyl) (C$_1$–C$_6$ alkyl), wherein each C$_1$–C$_6$ alkyl group is independently substituted with from 0 to 2 R$_6$;

the remaining R$_a$ and R$_b$ at each occurrence are independently selected from the group consisting of hydrogen, halogen, cyano, nitro, haloalkyl, haloalkoxy, hydroxy, amino, C$_1$–C$_6$ alkoxy substituted with 0–2 R$_6$, —NH(C$_1$–C$_6$ alkyl) wherein the C$_1$–C$_6$ alkyl group is substituted with 0–2 R$_6$, —N(C$_1$–C$_6$ alkyl) (C$_1$–C$_6$ alkyl) wherein the C$_1$–C$_6$ alkyl groups are independently substituted with 0–2 R$_6$, C$_1$–C$_6$ alkyl wherein the C$_1$–C$_6$ alkyl group is substituted with 0–2 R$_6$, phenyl substituted with 0–3 R$_6$, —XR$_7$, and Y;

W represents phenyl, thienyl, or pyridyl, wherein each is substituted with R$_{d}$, R$_{d'}$, and R$_{d''}$ which are independently selected from the group consisting of hydrogen, halogen, cyano, nitro, haloalkyl, haloalkoxy, hydroxy, amino, C$_1$–C$_6$ alkyl substituted with 0–2 R$_6$, C$_1$–C$_6$ alkoxy substituted with 0–2 R$_6$, —NH(C$_1$–C$_6$ alkyl) wherein the C$_1$–C$_6$ alkyl is substituted with 0–2 R$_6$, phenyl substituted with 0–3 R$_6$, —XR$_7$, Y, and —N(C$_1$–C$_6$ alkyl$_1$) (C$_1$–C$_6$ alkyl$_2$) wherein alkyl$_1$ and alkyl$_2$ are independently substituted with 0–2 R$_6$, or alkyl$_1$, alkyl$_2$ and the nitrogen to which they are attached form a heterocycloalkyl ring substituted with 0–2 R$_6$;

X at each occurrence is independently selected from the group consisting of —CH$_2$—, —CHR$_8$—, —O—, —S(O)$_m$—, —NH—, —NR$_8$—, —C(O)—, —C(O)O—, —C(O)NH—, —C(O)NR$_8$—, —S(O)$_m$NH—, —S(O)$_m$NR$_8$—, —NHC(O)—, —NR$_8$C(O)—, —NHS(O)$_m$—, and —NR$_8$S(O)$_m$—; wherein m is 0, 1, or 2;

R$_6$ at each occurrence is independently selected from the group consisting of halogen, hydroxy, C$_1$–C$_6$ alkyl, C$_1$–C$_6$ alkoxy, —NH(C$_1$–C$_6$ alkyl), —N(C$_1$–C$_6$ alkyl) (C$_1$–C$_6$ alkyl), —NH—(C$_1$–C$_6$ alkyl-Y), —N(C$_1$–C$_6$ alkyl)—(C$_1$–C$_6$ alkyl-Y), —NH—(C$_1$–C$_6$ alkyl-N (C$_1$–C$_6$ alkyl) (C$_1$–C$_6$ alkyl)), —N(C$_1$–C$_6$ alkyl)—(C$_1$–C$_6$ alkyl N(C$_1$–C$_6$ alkyl) (C$_1$–C$_6$ alkyl)), morpholinyl, pyrrolidinyl, piperidinyl, thiomorpholinyl, piperazinyl, homopiperazinyl, S(O)$^m$(C$_1$–C$_6$ alkyl), haloalkyl, haloalkoxy, —CO(C$_1$–C$_6$ alkyl), —CONH(C$_1$–C$_6$ alkyl), CON(C$_1$–C$_6$ alkyl) (C$_1$–C$_6$ alkyl), —XR$_7$, and Y; wherein
m is 0, 1, or 2;

R$_7$ and R$_8$ at each occurrence are independently C$_1$–C$_8$ alkyl, wherein R$_7$ and R$_8$ are substituted with 0, 1, 2, 3, or 4 substituents selected from the group consisting of oxo, hydroxy, halogen, amino, cyano, nitro, haloalkyl, haloalkoxy, C$_1$–C$_6$ alkoxy, —NH (C$_1$–C$_6$ alkyl), —N(C$_1$–C$_6$ alkyl) (C$_1$–C$_6$ alkyl), —NHC(O) (C$_1$–C$_6$ alkyl), —N(C$_1$–C$_6$ alkyl)C(O) (C$_1$–C$_6$ alkyl), —NHS(O)$_m$(C$_1$–C$_6$ alkyl), —S(O)m(C$_1$–C$_6$ alkyl), S(O)$_m$NH(C$_1$–C$_6$ alkyl), and —S(O)$_m$N(C$_1$–C$_6$ alkyl) (C$_1$–C$_6$ alkyl), and Y';
wherein m is 0, 1, or 2; and Y and Y' at each occurrence are independently selected from 5- to 8-membered carbocycles and heterocycles, which are saturated, partially unsaturated, or aromatic, and contain zero, one or two heteroatoms selected from N, O, and S, and which carbocycles and heterocycles may be further substituted with 1, 2, 3, or 4 substituents selected from the group consisting of halogen, oxo, hydroxy, amino, nitro, cyano, C$_1$–C$_6$ alkyl, C$_1$–C$_6$ alkoxy, —NH(C$_1$–C$_6$ alkyl), —N(C$_1$–C$_6$ alkyl) (C$_1$–C$_6$ alkyl), and —S(O)$_a$(C$_1$–C$_6$ alkyl); wherein a is 0, 1, or 2.

3. A compound or salt according to claim 1 of the formula:

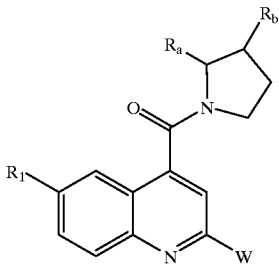

wherein $R_1$, $R_a$, $R_b$, and W are defined as in claim 1.

4. A compound or salt according to claim 3 wherein
$R_1$ is hydrogen, halogen, $C_1$–$C_2$alkyl or $C_1$–$C_2$alkoxy;
$R_a$ is selected from hydrogen, halogen, $C_1$–$C_6$ alkyl, $C_1$–$C_6$alkoxy, haloalkyl, haloalkoxy, hydroxy $C_1$–$C_6$alkyl, mono- or di-($C_1$–$C_6$)alkylamino, mono- or di-($C_1$–$C_6$) alkyl$_3$amino($C_1$–$C_6$)alkyl where each alkyl$_3$ is optionally substituted by mono- or di ($C_1$–$C_6$) alkylamino, heterocycloalkyl ($C_1$–$C_6$)alkyl, heterocycloalkyl ($C_1$–$C_6$) alkylamino, or heterocycloalkyl which is optionally substituted by $C_1$–$C_6$alkyl;
$R_b$ is selected from hydrogen, halogen, hydroxy, methyl, and ethyl;
With the proviso that at least one of $R_a$ and $R_b$ is not hydrogen; and
W is phenyl, pyridyl, or thienyl, each of which is substituted with $R_d$, $R_{d'}$, and $R_{d''}$, where $R_d$, $R_{d'}$, and $R_{d''}$ are independently selected from hydrogen, halogen, hydroxy, haloalkyl, di($C_1$–$C_6$)alkylamino ($C_1$–$C_6$)alkoxy, $C_1$–$C_6$ alkyl, $C_1$–$C_6$ alkoxy, mono- or di-($C_1$–$C_6$)alkylamino, $C_1$–$C_6$ alkylamino($C_1$–$C_6$) alkoxy, $C_3$–$C_7$ cycloalkylamino($C_1$–$C_6$) alkoxy, and heteroaryl ($C_1$–$C_6$) alkoxy.

5. A compound or salt of claim 4 wherein $R_d$, $R_{d'}$, and $R_{d''}$ are independently hydrogen, fluorine or hydroxyl.

6. A compound or salt according to claim 4, wherein W is phenyl carrying $R_d$, $R_{d'}$, and $R_{d''}$ where one of $R_d$, $R_{d'}$, and $R_{d''}$ is hydrogen and the other two are independently hydrogen, haloalkyl, haloalkoxy $C_1$–$C_6$ alkyl, $C_1$–$C_6$ alkoxy, mono- or di-($C_1$–$C_6$)alkylamino, $C_1$–$C_6$ alkylamino ($C_1$–$C_6$)alkoxy, $C_3$–$C_7$ cycloalkylamino($C_1$–$C_6$) alkoxy, or heteroaryl($C_1$–$C_6$) alkoxy.

7. A compound or salt of claim 6 wherein $R_a$ is hydrogen, hydroxy($C_1$–$C_6$)alkyl, 4-($C_1$–$C_6$)alkyl-[1,4]diazepan-1-yl ($C_1$–$C_6$)alkyl, 4- ($C_1$–$C_6$)alkyl-piperazin-1-yl ($C_1$–$C_6$)alkyl, mono- or di ($C_1$–$C_6$)alkylamino($C_1$–$C_6$)alkyl(($C_1$–$C_6$)alkyl)amino($C_1$–$C_6$)alkyl, mono- or di(($C_1$–$C_6$)alkylamino($C_1$–$C_6$) alkylamino($C_1$–$C_6$)alkyl, or pyrrolidin-1-yl or piperidin-1-yl($C_1$–$C_6$)alkylamino($C_1$–$C_6$)alkyl.

8. A compound or salt of claim 6 wherein $R_a$ is hydroxymethyl.

9. A compound or salt according to claim 1
wherein W is phenyl or thienyl, each of which is optionally mono- or disubstituted with groups independently selected from $C_1$–$C_6$ alkyl, $C_1$–$C_6$ alkoxy, halogen, hydroxy, haloalkyl, haloalkoxy, mono- or di- ($C_1$–$C_6$) alkylamino, $C_1$–$C_6$ alkylamino($C_1$–$C_6$)alkoxy, $C_1$–$C_6$ alkoxy, $C_3$–$C_7$ cycloalkylamino($C_1$–$C_6$) alkoxy, and heteroaryl ($C_1$–$C_6$)alkoxy.

10. A compound or salt according to claim 1 of the formula:

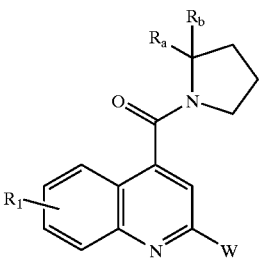

wherein $R_1$, $R_a$, and $R_b$, are defined as in claim 1 and
W is phenyl, pyridyl, or thienyl, each of which is substituted with $R_d$, $R_{d'}$, and $R_{d''}$ wherein
$R_d$, $R_{d'}$, and $R_{d''}$ are independently selected from the group consisting of hydrogen, halogen, cyano, nitro, haloalkyl, haloalkoxy, hydroxy, amino, and $C_1$–$C_6$ alkyl substituted with 0–2 $R_6$, $C_1$–$C_6$ alkoxy substituted with 0–2 $R_6$, —NH($C_{1-6}$ alkyl) substituted with 0–2 $R_6$, —N($C_1$–$C_6$ alkyl) ($C_1$–$C_6$ alkyl) wherein each alkyl is independently substituted with 0–2 $R_6$, —$XR_7$, and Y;
X at each occurrence is independently selected from the group consisting of —$CH_2$—, —$CHR_8$—, —O—, —NH—, and —$NR_8$—;
$R_6$ at each occurrence is independently selected from the group consisting of halogen, hydroxy, $C_1$–$C_6$ alkyl, $C_1$–$C_6$ alkoxy, —N($C_1$–$C_6$ alkyl) —N($C_1$–$C_6$ alkyl) ($C_1$–$C_6$ alkyl), —NH($C_1$–$C_6$ alkyl-Y), —N($C_1$–$C_6$ alkyl)—($C_1$–$C_6$ alkyl-Y), —NH—($C_1$–$C_6$ alkyl-N ($C_1$–$C_6$ alkyl) ($C_1$–$C_6$ alkyl)), —N($C_1$–$C_6$ alkyl)—($C_1$–$C_6$ alkyl-N($C_1$–$C_6$ alkyl) ($C_1$–$C_6$ alkyl)), morpholinyl, pyrrolidinyl, piperidinyl, thiomorpholinyl, piperazinyl, homopiperazinyl, —$S(O)_m$($C_1$–$C_6$ alkyl), haloalkyl, haloalkoxy, —CO ($C_1$–$C_6$ alkyl), —CONH($C_1$–$C_6$ alkyl), CON($C_1$–$C_6$ alkyl) ($C_1$–$C_6$ alkyl), —$XR_7$, and Y; wherein
m is 0, 1, or 2;
$R_7$ and $R_8$ at each occurrence are independently $C_1$–$C_8$ alkyl, wherein $R_7$ and $R_8$ are substituted with 0, 1, 2, 3, or 4 substituents selected from the group consisting of oxo, hydroxy, halogen, amino, cyano, nitro, haloalkyl, haloalkoxy, $C_1$–$C_6$ alkoxy, —NH ($C_1$–$C_6$ alkyl), —N($C_1$–$C_6$ alkyl) ($C_1$–$C_6$ alkyl); and
Y at each occurrence is independently selected from 5- to 8-membered carbocycles and heterocycles, which are saturated, partially unsaturated, or aromatic and contain zero, one or two heteroatom(s) selected from N, O, and S, and which carbocycles and heterocycles are optionally further substituted with one or more substituents selected from halogen, oxo, hydroxy, amino, nitro, cyano, $C_1$–$C_6$ alkyl, $C_1$–$C_6$ alkoxy, and mono- or di $C_1$–$C_6$ alkylamino.

11. A compound or salt according to claim 3 wherein $R_b$ is hydrogen; and W is phenyl or thienyl each of which is substituted with $R_d$, $R_{d'}$, and $R_{d''}$ where $R_d$, $R_{d'}$, and $R_{d''}$ are independently selected from the group consisting of hydrogen, halogen, cyano, nitro, haloalkyl, haloalkoxy, hydroxy, amino, and $C_1$–$C_6$ alkyl substituted with 0–2 $R_6$, $C_1$–$C_6$ alkoxy substituted with 0–2 $R_6$, —NH($C_{1-6}$ alkyl) substituted with 0–2 $R_6$, —N($C_1$–$C_6$ alkyl) ($C_1$–$C_6$ alkyl) wherein each alkyl is independently substituted with 0–2 $R_6$, —$XR_7$, and Y;
X at each occurrence is independently selected from the group consisting of —$CH_2$, —$CHR_8$—, —O—, —NH—, and —$NR_8$—;

R₆ at each occurrence is independently selected from the group consisting of halogen, hydroxy, $C_1$–$C_6$ alkyl, $C_1$–$C_6$ alkoxy, —NH($C_1$–$C_6$ alkyl), —N($C_1$–$C_6$ alkyl)($C_1$–$C_6$ alkyl), —NH—($C_1$–$C_6$ alkyl-Y), —N($C_1$–$C_6$ alkyl)—($C_1$–$C_6$ alkyl-Y) —NH—($C_1$–$C_6$ alkyl—N ($C_1$–$C_6$ alkyl) ($C_1$–$C_6$ alkyl)), —N($C_1$–$C_6$ alkyl)—($C_1$–$C_6$ alkyl), —N($C_1$–$C_6$ alkyl) ($C_1$–$C_6$ alkyl)), morpholinyl, pyrrolidinyl, piperidinyl, thiomorpholinyl, piperazinyl, homopiperazinyl, -S(O)m($C_1$–$C_6$ alkyl), haloalkyl, haloalkoxy, —CO($C_1$–$C_6$ alkyl), —CONH($C_1$–$C_6$ alkyl), CON($C_1$–$C_6$ alkyl) ($C_1$–$C_6$ alkyl), —XR₇, and Y; wherein
m is 0, 1, or 2;

R₇ and R₈ at each occurrence are independently $C_1$–$C_8$ alkyl, wherein R₇ and R₈ are substituted with 0, 1, 2, 3, or 4 substituents selected from the group consisting of oxo, hydroxy, halogen, amino, cyano, nitro, haloalkyl, haloalkoxy, $C_1$–$C_6$ alkoxy, —NH($C_1$–$C_6$ alkyl), and —N($C_1$–$C_6$alkyl) ($C_1$–$C_6$ alkyl); and Y at each occurrence is independently selected from 5- to 8-membered carbocycles and heterocycles, which are saturated, partially unsaturated, or aromatic and contain zero, one or two heteroatom(s) selected from N, O, and S, and which carbocycles and heterocycles may be further substituted with one or more substituents selected from halogen, oxo, hydroxy, amino, nitro, cyano, $C_1$–$C_6$ alkyl, $C_1$–$C_6$ alkoxy, and mono- or di $C_1$–$C_6$ alkylamino.

12. A compound or salt according to claim 11 wherein is hydroxymethyl and $R_b$ is hydrogen.

13. A compound according to claim 1, which is selected from
1-[[2-(3-Fluoro-4-methoxyphenyl)-4-quinolinyl]carbonyl]pyrrolidine;
1-[[2-(2-Methylphenyl)-4-quinolinyl]carbonyl]-pyrrolidine;
1-[[2-[4-(3-piperidinylamino-1-propoxy)phenyl]-4-quinolinyl]carbonyl]pyrrolidine;
1-[[2-(4-(3-Diethylamino-1-propoxy)phenyl]-4-quinolinyl]carbonyl]pyrrolidine;
(R)-1-[[G-Fluoro-2-(4-fluorophenyl)-4-quinolinyl]carbonyl]-2-hydroxymethylpyrrolidine;
(R)-1-[[2-(4-Fluorophenyl)-4-quinolinyl]carbonyl]-2-hydroxymethyl-pyrrolidine;
(R)-1-[[2-(3,4-Difluorophenyl)-4-quinolinyl]carbonyl]-2-hydroxymethylpyrrolidine;
(R)-1-[(6—Chloro-2-phenyl-4-quinolinyl)carbonyl]-2-hydroxymethylpyrrolidine; and
(R)-1-[[2-(3—Chloro-4-fluorophenyl)-4-quinolinyl]carbonyl]-2-hydroxymethylpyrrolidine; and the pharmaceutically acceptable salts thereof.

14. A compound according to claim 1, which is selected from
(R)-1-[[6-Fluoro-2-(3,4-difluorophenyl)-4 -quinolinyl)carbonyl]-2-hydroxymethylpyrrolidine;
(R)-1-[[2-(4-Methoxyphenyl)-4-quinolinyl]carbonyl]-2-hydroxymethylpyrrolidine;
(R)-1-[[6-Fluoro-2-(4-fluorophenyl)-4-quinolinyl)carbonyl]-2-hydroxymethyl-pyrrolidine;
(R)-1-[[2-(3-Methoxyphenyl)-4-quinolinyl]carbonyl]-2-hydroxymethyl-pyrrolidine;
(R)-1-[(6-Fluoro-2-phenyl-4-quinolinyl)carbonyl]-2-hydroxymethyl-pyrrolidine;
(R)-1-[[2-(2-Fluorophenyl)-4-quinolinyl]carbonyl]-2-hydroxymethyl-pyrrolidine;
(R)-1-[[2-(2-Methylphenyl)-4-quinolinyl]carbonyl]-2-hydroxymethyl-pyrrolidine;
(R)-1-[[6-Fluoro-2-(2-fluorophenyl)-4-quinolinyl)carbonyl]-2-hydroxymethyl-pyrrolidine;
(R)-1-[[6-Fluoro-2-(3-thienyl)-4-quinolinyl)carbonyl]-2-hydroxymethyl-pyrrolidine; and
(R)-1-[[2-Phenyl-4-quinolinyl]carbonyl]-2-hydroxymethyl-pyrrolidine; and the pharmaceutically acceptable salts thereof.

15. A compound according to claim 1, which is selected from
(R)-1-[[2-(2-Fluoro-4-hydroxyphenyl)-4-quinolinyl]carbonyl]-2-hydroxymethyl-pyrrolidine;
(R)-1-[[2-(2,4-Difluorophenyl)-4-quinolinyl]carbonyl]-2-hydroxymethyl-pyrrolidine;
(R)-1-[[2-(2-Fluoro-4-ethoxyphenyl)-4-quinolinyl]carbonyl]-2-hydroxymethyl-pyrrolidine;
(R)-1-[[2-(2,6-Difluorophenyl)-4-quinolinyl]carbonyl]-2-hydroxymethyl-pyrrolidine;
(R)-1-[[6-Bromo-2-phenyl-4-quinolinyl)carbonyl]-2-hydroxymethyl-pyrrolidine;
(R)-1- [[2- [2-Fluoro-4-(3-bromo-1-propoxy)phenyl]-4-quinolinyl]carbonyl]-2-hydroxymethyl-pyrrolidine;
(R)-1-[[2-(2-Fluoro-4-methoxyphenyl)-4 -quinolinyl]carbonyl]-2-hydroxymethylpyrrolidine;
(R)-1-[[2-(2,5-Difluorophenyl)-4-quinolinyl]carbonyl]-2-hydroxymethylpyrrolidine;
(R)-1- [[6-Methoxy-2-phenyl-4-quinolinyl)carbonyl]-2-hydroxymethylpyrrolidine;
(R)-1-[[6—Chloro-2-(2-fluoro-4-methoxyphenyl)-4-quinolinyl]carbonyl]-2-hydroxymethylpyrrolidine;
(R)-1-[[2-(3,4-Difluorophenyl)-4-quinolinyl]carbonyl]-2-(2 -diethylamino-1-ethyl-1-methyl-aminomethyl)pyrrolidine; and
(R)-1-[[2-(3,4-Difluorophenyl)-4-quinolinyl]carbonyl]-2-(N-ethylpiperazinyl)methyl)pyrrolidine; and the pharmaceutically acceptable salts thereof.

16. A compound according to claim 1, which is selected from
(R)-1-[[2-(3,4-Difluorophenyl)-4-quinolinyl]carbonyl]-2-(2 -diethylamino-1-ethyl-1-ethyl-aminomethyl)pyrrolidine;
(R)-1-[[2-(3,4-Difluorophenyl)-4-quinolinyl]carbonyl]-2-(2 -diethylaminoethyl)-aminomethyl)pyrrolidine;
(R)-1-[[2-(3,4-Difluorophenyl)-4-quinolinyl]carbonyl]-2-(2 -dimethylamino-1-ethyl-1-methyl-aminomethyl)pyrrolidine;
(R)-1-[[2-(4-Fluorophenyl)-4-quinolinyl]carbonyl]-2-(2 -dimethylaminoethyl)aminomethyl)pyrrolidine;
(R)-1-[[2-(3,4-Difluorophenyl)-4-quinolinyl]carbonyl]-2-(N-methylhomopiperazinyl)methyl)pyrrolidine;
(R)-1-[[2-(3,4-Difluorophenyl)-4-quinolinyl]carbonyl]-2-(N-methylpiperazinyl)methyl)pyrrolidine;
(R)-1-[[2-(3,4-Difluorophenyl)-4-quinolinyl]carbonyl]-2-(N-piperidinylethylaminomethyl)pyrrolidine;
(R)-1-[[2-(3,4-Difluorophenyl)-4-quinolinyl]carbonyl]-2-(N-pyrrolidinylethylaminomethyl)pyrrolidine;
(R)-1-[(2-phenyl-4-quinolinyl)carbonyl]-2-hydroxymethyl pyrrolidine; and
1-[[2-(4-Fluorophenyl)-4-quinolinyl]carbonyl]-3-hydroxy-pyrrolidine; and the pharmaceutically acceptable salts thereof.

17. A compound according to claim 1, which is selected from

1-[(2-phenylthieno[3,2-b]pyridyl)carbonyl]-pyrrolidine;
(R)-1-[(2-phenylthieno[3,2-b]pyridyl)carbonyl]-2-hydroxymethyl-pyrrolidine; and
1-[(2-phenyl-1,6-naphthyridinyl)carbonyl]-pyrrolidine; and the pharmaceutically acceptable salts thereof.

18. A compound according to claim 1, which is selected from (S)-1-[[6-Fluoro-2-(4-fluorophenyl)-4-quinolinyl]carbonyl]-2-hydroxymethylpyrrolidine;
(S)-1-[[2-(4-Fluorophenyl)-4-quinolinyl]carbonyl]-2-hydroxymethyl-pyrrolidine;
(S)-1-[[2-(3,4-Difluorophenyl)-4-quinolinyl]carbonyl]-2-hydroxymethylpyrrolidine;
(S)-1-[(6—Chloro-2-phenyl-4-quinolinyl)carbonyl]-2-hydroxymethylpyrrolidine; and
(S)-1-[[2-(3—Chloro-4-fluorophenyl)-4-quinolinyl]carbonyl]-2-hydroxymethylpyrrolidine; and the pharmaceutically acceptable salts thereof.

19. A compound according to claim 1, which is selected from (S)-1-[[6-Fluoro-2-(3,4-difluorophenyl)-4 -quinolinyl)carbonyl]-2-hydroxymethylpyrrolidine;
(S)-1-[[2-(4-Methoxyphenyl)-4-quinolinyl]carbonyl]-2-hydroxymethylpyrrolidine;
(S) -1- [[6-Fluoro-2-(4-fluorophenyl)-4-quinolinyl)carbonyl]-2-hydroxymethyl-pyrrolidine;
(S)-1-[[2-(3-Methoxyphenyl)-4-quinolinyl]carbonyl]-2-hydroxymethyl-pyrrolidine;
(S)-1-[(6-Fluoro-2-phenyl-4-quinolinyl)carbonyl]-2-hydroxymethyl-pyrrolidine;
(S)-1-[[2-(2-Fluorophenyl)-4-quinolinyl]carbonyl]-2-hydroxymethyl-pyrrolidine;
(S)-1-[[2-(2-Methylphenyl)-4-quinolinyl]carbonyl]-2-hydroxymethyl-pyrrolidine;
(S)-1-[[6-Fluoro-2-(2-fluorophenyl)-4-quinolinyl)carbonyl]-2-hydroxymethyl-pyrrolidine;
(S)-1-[[6-Fluoro-2-(3-thienyl)-4-quinolinyl)carbonyl]-2-hydroxymethyl-pyrrolidine; and
(S)-1-[[2-Phenyl-4-quinolinyl]carbonyl]-2-hydroxymethyl-pyrrolidine; and the pharmaceutically acceptable salts thereof.

20. A compound according to claim 1, which is selected from (S)-1-[[2-(2-Fluoro-4-hydroxyphenyl)-4-quinolinyl]carbonyl]-2-hydroxymethyl-pyrrolidine;
(S)-1-[[2-(2,4-Difluorophenyl)-4-quinolinyl]carbonyl]-2-hydroxymethyl-pyrrolidine;
(S)-1-[[2-(2-Fluoro-4-ethoxyphenyl)-4-quinolinyl]carbonyl]-2-hydroxymethyl-pyrrolidine;
(S)-1-[[2-(2,6-Difluorophenyl)-4-quinolinyl]carbonyl]-2-hydroxymethyl-pyrrolidine;
(S)-1-[[6-Bromo-2-phenyl-4-quinolinyl)carbonyl]-2-hydroxymethyl-pyrrolidine;
(S)-1-[[2-[2-Fluoro-4-(3-bromo-i-propoxy)phenyl)-4-quinolinyl]carbonyl]-2-hydroxymethyl-pyrrolidine;
(S)-1-[[2-(2-Fluoro-4-methoxyphenyl)-4 -quinolinyl]carbonyl]-2-hydroxymethylpyrrolidine;
(S)-1- [[2-(2,5-Difluorophenyl)-4-quinolinyl]carbonyl]-2-hydroxymethylpyrrolidine;
(S)-1-[[6-Methoxy-2-phenyl-4-quinolinyl)carbonyl]-2-hydroxymethylpyrrolidine;
(S)-1-[[6—Chloro-2-(2-fluoro-4-methoxyphenyl)-4-quinolinyl]carbonyl]-2-hydroxymethylpyrrolidine;
(S)-1-[[2-(3,4-Difluorophenyl)-4-quinolinyl]carbonyl]-2-(2 -diethylamino-1-ethyl-1-methyl-aminomethyl)pyrrolidine; and
(S)-1-[[2-(3,4-Difluorophenyl)-4-quinolinyl]carbonyl]-2-(N-ethylpiperazinyl)methyl)pyrrolidine; and the pharmaceutically acceptable salts thereof.

21. A compound according to claim 1, which is selected from (S)-1-[[2-(3,4-Difluorophenyl)-4-quinolinyl]carbonyl]-2-(2-diethylamino-1-ethyl-1-ethyl-aminomethyl)pyrrolidine;

(S)-1-[[2-(3,4-Difluorophenyl)-4-quinolinyl]carbonyl]-2-(2 -diethylaminoethyl)-aminomethyl)pyrrolidine;
(S)-1-[[2-(3,4-Difluorophenyl)-4-quinolinyl]carbonyl]-2-(2 -dimethylamino-1-ethyl-1-methyl-aminomethyl)pyrrolidine;
(S)-1-[[2-(4-Fluorophenyl)-4-quinolinyl]carbonyl]-2-(2-dimethylaminoethyl)aminomethyl)pyrrolidine;
(S)-1-[[2-(3,4-Difluorophenyl)-4-quinolinyl]carbonyl]-2-(N-methylhomopiperazinyl)methyl)pyrrolidine;
(S)-1-[[2-(3,4-Difluorophenyl)-4-quinolinyl]carbonyl]-2-(N-methylpiperazinyl)methyl)pyrrolidine;
(S)-1-[[2-(3,4-Difluorophenyl)-4-quinolinyl]carbonyl]-2-(N-piperidinylethylaminomethyl)pyrrolidine;
(S)-1-[[2-(3,4-Difluorophenyl)-4-quinolinyl]carbonyl]-2-(N-pyrrolidinylethylaminomethyl)pyrrolidine;
(S)-1-[(2-phenyl-4-quinolinyl)carbonyl]-2-hydroxymethyl pyrrolidine; and
(S)-1- [(2-phenylthieno[3,2-b]pyridyl)carbonyl]-2-hydroxymethyl-pyrrolidine; and the pharmaceutically acceptable salts thereof.

22. A compound according to claim 1, which is selected from (±)-1-[[6-Fluoro-2-(4-fluorophenyl)-4-quinolinyl]carbonyl]-2-hydroxymethylpyrrolidine;
(±)-1-[[2-(4-Fluorophenyl)-4-quinolinyl]carbonyl]-2-hydroxymethyl-pyrrolidine;
(±)-1-[[2-(3,4-Difluorophenyl)-4-quinolinyl]carbonyl]-2-hydroxymethylpyrrolidine;
(±)-1-[(6—Chloro-2-phenyl-4-quinolinyl)carbonyl]-2-hydroxymethylpyrrolidine; and
(±)-1-[[2-(3—Chloro-4-fluorophenyl)-4-quinolinyl]carbonyl]-2-hydroxymethylpyrrolidine; and the pharmaceutically acceptable salts thereof.

23. A compound according to claim 1, which is selected from (±)-1-[[6-Fluoro-2-(3,4-difluorophenyl)-4 -quinolinyl)carbonyl]-2-hydroxymethylpyrrolidine;
(±)-1-[[2-(4-Methoxyphenyl)-4-quinolinyl]carbonyl]-2-hydroxymethylpyrrolidine;
(±)-1-[[6-Fluoro-2-(4-fluorophenyl)-4-quinolinyl)carbonyl]-2-hydroxymethyl-pyrrolidine;
(±)-1-[[2-(3-Methoxyphenyl)-4-quinolinyl]carbonyl]-2-hydroxymethyl-pyrrolidine;
(±)-1-[(6-Fluoro-2-phenyl-4-quinolinyl)carbonyl]-2-hydroxymethyl-pyrrolidine;
(±)-1-[[2-(2-Fluorophenyl)-4-quinolinyl]carbonyl]-2-hydroxymethyl-pyrrolidine;
(±)-1-[[2-(2-Methylphenyl)-4-quinolinyl]carbonyl]-2-hydroxymethyl-pyrrolidine;
(±)-1-[[6-Fluoro-2-(2-fluorophenyl)-4-quinolinyl)carbonyl]-2-hydroxymethyl-pyrrolidine;

(±)-1-[[6-Fluoro-2-(3-thienyl)-4-quinolinyl)carbonyl]-2
-hydroxymethyl-pyrrolidine; and
(±)-1-[[2-Phenyl-4-quinolinyl]carbonyl]-2-
hydroxymethyl-pyrrolidine; and the pharmaceutically
acceptable salts thereof.

24. A compound according to claim 1, which is selected from
(±)-1-[[2-(2-Fluoro-4-hydroxyphenyl)-4-quinolinyl]
carbonyl]-2-hydroxymethyl-pyrrolidine;
(±)-1-[[2-(2,4-Difluorophenyl)-4-quinolinyl]carbonyl]-2
-hydroxymethyl-pyrrolidine;
(±)-1-[[2-(2-Fluoro-4-ethoxyphenyl)-4-quinolinyl]
carbonyl]-2-hydroxymethyl-pyrrolidine;
(±)-1-[[2-(2,6-Difluorophenyl)-4-quinolinyl]carbonyl]-2
-hydroxymethyl-pyrrolidine;
(±)-1-[[6-Bromo-2-phenyl-4-quinolinyl)carbonyl]-2
-hydroxymethyl-pyrrolidine;
(±)-1-[[2-[2-Fluoro-4-(3-bromo-1-propoxy)phenyl)-4
-quinolinyl]carbonyl]-2-hydroxymethyl-pyrrolidine;
(±)-1-[[2-(2-Fluoro-4-methoxyphenyl)-4 -quinolinyl]
carbonyl]-2-hydroxymethylpyrrolidine;
(±)-1-[[2-(2,5-Difluorophenyl)-4-quinolinyl]carbonyl]-2
-hydroxymethylpyrrolidine;
(±)-1-[[6-Methoxy-2-phenyl-4-quinolinyl)carbonyl]-2
-hydroxymethylpyrrolidine;
(±)-1-[[6—Chloro-2-(2-fluoro-4-methoxyphenyl)-4
-quinolinyl]carbonyl]-2-hydroxymethylpyrrolidine;
(±)-1-[[2-(3,4-Difluorophenyl)-4-quinolinyl]carbonyl]-
2-(2 -diethylamino-1-ethyl-1-methyl-aminomethyl)
pyrrolidine; and
(±)-1-[[2-(3,4-Difluorophenyl)-4-quinolinyl]carbonyl]-2
-(N-ethylpiperazinyl)methyl)pyrrolidine; and the pharmaceutically acceptable salts thereof.

25. A compound according to claim 1, which is selected from (±)-1-[[2-(3,4-Difluorophenyl)-4-quinolinyl]
carbonyl]-2-(2-diethylamino-1-ethyl-1-ethyl-aminomethyl)
pyrrolidine;
(±)-1-[[2-(3,4-Difluorophenyl)-4-quinolinyl]carbonyl]-
2-(2 -diethylaminoethyl)-aminomethyl)pyrrolidine;
(±)-1-[[2-(3,4-Difluorophenyl)-4-quinolinyl]carbonyl]-
2-(2 -dimethylamino-1-ethyl-1-methyl-aminomethyl)
pyrrolidine;
(±)-1-[[2-(4-Fluorophenyl)-4-quinolinyl]carbonyl]-2-(2
-dimethylaminoethyl)aminomethyl)pyrrolidine;
(±)-1-[[2-(3,4-Difluorophenyl)-4-quinolinyl]carbonyl]-2
-(N-methylhomopiperazinyl)methyl)pyrrolidine;
(±)-1-[[2-(3,4-Difluorophenyl)-4-quinolinyl]carbonyl]-2
-(N-methylpiperazinyl)methyl)pyrrolidine;
(±)-1-[[2-(3,4-Difluorophenyl)-4-quinolinyl]carbonyl]-2
-(N-piperidinylethylaminomethyl)pyrrolidine;
(±)-1-[[2-(3,4-Difluorophenyl)-4-quinolinyl]carbonyl]-2
-(N-pyrrolidinylethylaminomethyl)pyrrolidine;
(±)-1-[(2-phenyl-4-quinolinyl)carbonyl]-2-
hydroxymethyl pyrrolidine; and
(±)-1-[(2-phenylthieno[3,2-b]pyridyl)carbonyl]-2
-hydroxymethyl-pyrrolidine; and the pharmaceutically
acceptable salts thereof.

26. A pharmaceutical composition comprising a compound or salt according to claim 1 combined with at least one pharmaceutically acceptable carrier or excipient.

27. A compound or salt according to claim 1 of the formula:

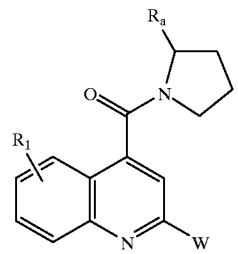

wherein $R_a$ and W are defined as in claim 1; and
$R_1$ is selected from the group consisting of hydrogen, halogen, hydroxy, $C_1$–$C_6$ alkoxy, and $C_1$–$C_6$ alkyl.

28. A compound or salt according to claim 1 of the formula:

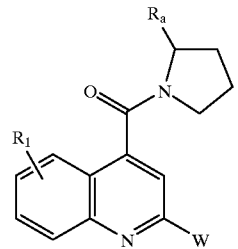

wherein W is defined as in claim 1;
$R_1$ is selected from the group consisting of hydrogen, halogen, hydroxy, $C_1$–$C_6$ alkoxy, and $C_1$–$C_6$ alkyl;
$R_a$ is selected from the group consisting of —$XR_7$, and $C_1$–$C_6$ alkyl, wherein the $C_1$–$C_6$ alkyl is optionally substituted with 0, 1, or 2 $R_6$;
$R_6$ is selected from the group consisting of —NH—($C_1$–$C_6$ alkyl-Y), —N($C_1$–$C_6$ alkyl)-($C_1$–$C_6$ alkyl-Y), —NH—($C_1$–$C_6$ alkyl—N($C_1$–$C_6$ alkyl) ($C_1$–$C_6$ alkyl)), and —N($C_1$–$C_6$ alkyl)-($C_1$–$C_6$ alkyl—N ($C_1$–$C_6$ alkyl) ($C_1$–$C_6$ alkyl));
X is selected from the group consisting of —$CH_2$—, —$CHR_8$—, —C(O)—, —C(O)O—, —C(O)NH—, —C(O)N($C_1$–$C_6$ alkyl)-, and —C(O)N($C_1$–$C_6$ alkyl) ($C_1$–$C_6$ alkyl)-;
$R_7$ and $R_8$ at each occurrence are independently $C_1$–$C_6$ alkyl optionally substituted with 1, 2, 3, or 4 substituents selected from the group consisting of hydroxy, amino, —NH($C_1$–$C_8$ alkyl), —NH($C_1$–$C_6$ alkyl) ($C_1$–$C_8$ alkyl); and
Y is selected from 5- to 8-membered carbocycles and heterocycles, which are saturated, partially unsaturated, or aromatic and contain zero, one or two heteroatoms selected from N, O, and S, which carbocycles and heterocycles are optionally further substituted with 1, 2, 3, or 4 substituents selected from the group consisting of halogen, oxo, hydroxy, amino, nitro, cyano, alkyl, $C_1$–$C_6$ alkoxy, —NH($C_1$–$C_6$ alkyl), —N($C_1$–$C_6$ alkyl) ($C_1$–$C_6$ alkyl), and —S(O)$_a$($C_1$–$C_6$ alkyl); wherein a is 0, 1, or 2.

29. A compound or salt according to claim 1 of the formula:

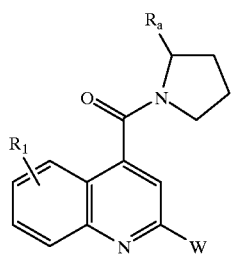

wherein
- R₁ is selected from the group consisting of hydrogen, halogen, hydroxy, $C_1$–$C_6$ alkoxy, and $C_1$–$C_6$ alkyl;
- $R_a$ is selected from the group consisting of —XR₇, and $C_1$–$C_6$ alkyl, wherein the $C_1$–$C_6$ alkyl is optionally substituted with 0, 1, or 2 R₆;
  - R₆ is selected from the group consisting of —NH—($C_1$–$C_6$ alkyl-Y), —N($C_1$–$C_6$ alkyl)-($C_1$–$C_6$ alkyl-Y), —NH—($C_1$–$C_6$ alkyl—N($C_1$–$C_6$ alkyl) ($C_1$–$C_6$ alkyl)), and —N($C_1$–$C_6$ alkyl)-($C_1$–$C_6$ alkyl—N($C_1$–$C_6$ alkyl) ($C_1$–$C_6$ alkyl));
- X is selected from the group consisting of —CH₂—, —CHR₈—, —C(O)—, —C(O)O—, —C(O)NH—, —C(O)N($C_1$–$C_6$ alkyl)-, and —C(O)N($C_1$–$C_6$ alkyl) ($C_1$–$C_6$ alkyl)-; and
- R₇ and R₈ at each occurrence are independently $C_1$–$C_6$ alkyl optionally substituted with 1, 2, 3, or 4 substituents selected from the group consisting of hydroxy, amino, —NH($C_1$–$C_8$ alkyl), —NH($C_1$–$C_8$ alkyl) ($C_1$–$C_8$ alkyl);
- W is thienyl or phenyl, wherein each is unsubstituted or substituted with 1, 2, or 3 substituents selected from the group consisting of halogen, hydroxy, $C_1$–$C_6$ alkoxy, optionally substituted with amino, NH($C_1$–$C_6$ alkyl), NH($C_3$–$C_6$ cycloalkyl), halogen, and Y; and
- Y is selected from 5- to 8-membered carbocycles and heterocycles, which are saturated, partially unsaturated, or aromatic and contain zero, one or two heteroatoms selected from N, O, and S, which carbocycles and heterocycles are optionally further substituted with 1, 2, 3, or 4 substituents selected from the group consisting of halogen, oxo, hydroxy, amino, nitro, cyano, $C_1$–$C_6$ alkyl, $C_1$–$C_6$ alkoxy, —NH($C_1$–$C_6$ alkyl), —N($C_1$–$C_6$ alkyl) ($C_1$–$C_6$ alkyl), and —S(O)$_a$($C_1$–$C_6$ alkyl); wherein
- a is 0, 1, or 2.

30. A compound or salt of claim 6 wherein $R_a$ is hydrogen, hydroxymethyl, [(2-diethylamino-ethyl)-methyl-amino]methyl, or [(2-Diethylamino-ethyl)-methyl-amino]methyl.

31. A compound or salt according to claim 4, wherein W is phenyl carrying $R_d$, $R_d'$, and $R_d''$ where one of $R_d$, $R_d'$, and $R_d''$ is hydrogen and the other two are independently hydrogen, halogen, hydroxy, $C_1$–$C_6$ alkylamino($C_1$–$C_6$) alkoxy, $C_1$–$C_6$ or alkoxy.

* * * * *